(12) United States Patent
Dodo

(10) Patent No.: US 8,261,734 B2
(45) Date of Patent: Sep. 11, 2012

(54) HEAT GENERATING BODY, HEAT INSULATING METHOD USING THE SAME AND PACKAGING MATERIAL FOR DIE MOLDING HEAT GENERATION

(75) Inventor: Toshihiro Dodo, Kanagawa (JP)

(73) Assignee: Mycoal Co., Ltd., Tochigi-Shi (JP)

( * ) Notice: Subject to any disclaimer, the term of this patent is extended or adjusted under 35 U.S.C. 154(b) by 770 days.

(21) Appl. No.: 11/632,226

(22) PCT Filed: Jul. 14, 2005

(86) PCT No.: PCT/JP2005/013014
§ 371 (c)(1),
(2), (4) Date: Jul. 31, 2007

(87) PCT Pub. No.: WO2006/006661
PCT Pub. Date: Jan. 19, 2006

(65) Prior Publication Data
US 2008/0029079 A1 Feb. 7, 2008

(30) Foreign Application Priority Data
Jul. 14, 2004 (JP) .................................. 2004-207842

(51) Int. Cl.
*A61F 7/00* (2006.01)
(52) U.S. Cl. .................... 126/204; 126/206; 126/263.01; 126/263.02; 607/112
(58) Field of Classification Search ............. 126/263.01, 126/263.02, 263.05, 263.07, 204, 206; 607/109, 607/96
See application file for complete search history.

(56) References Cited

U.S. PATENT DOCUMENTS

| 5,046,479 | A | | 9/1991 | Usui |
| 5,084,986 | A | | 2/1992 | Usui |
| 5,837,005 | A | * | 11/1998 | Viltro et al. .................... 607/112 |
| 6,096,067 | A | * | 8/2000 | Cramer et al. .................. 607/96 |

(Continued)

FOREIGN PATENT DOCUMENTS
EP   1229097   8/2002
(Continued)

OTHER PUBLICATIONS

U.S. Appl. No. 10/450,441, filed May 4, 2004, Usui et al.

(Continued)

*Primary Examiner* — Kenneth Rinehart
*Assistant Examiner* — Jorge Pereiro
(74) *Attorney, Agent, or Firm* — Kratz, Quintos & Hanson, LLP

(57) ABSTRACT

A heat generating body including a a moldable heat generating composition containing surplus water as a connecting substance interposed and heat sealed between packaging materials, which is characterized in that the packaging materials are each constituted of a substrate and a covering material; that the substrate is substantially planar and does not have an accommodating pocket; that the packaging materials each has a bending resistance of not more than 100 mm; that the packaging materials are each a non-elastic body at least at a temperature between 25° C. and 60° C., has a breaking strength of 500 g/mm$^2$ or more at 25° C. and has a breaking elongation of 30% or more at 90° C. The heat generating body is suitable for relaxation of symptoms of menstrual pain.

8 Claims, 6 Drawing Sheets

U.S. PATENT DOCUMENTS

| | | | |
|---|---|---|---|
| 6,146,732 A * | 11/2000 | Davis et al. | 428/64.1 |
| 6,336,935 B1 * | 1/2002 | Davis et al. | 607/112 |
| 6,436,128 B1 | 8/2002 | Usui | 607/96 |
| 6,863,682 B2 * | 3/2005 | Usui | 607/96 |
| 2004/0042965 A1 * | 3/2004 | Usui et al. | 424/40 |
| 2006/0154006 A1 | 7/2006 | Usui et al. | |

FOREIGN PATENT DOCUMENTS

| | | |
|---|---|---|
| EP | 1332741 | 10/2003 |
| JP | 11-89869 | 4/1999 |
| JP | 11-508786 | 8/1999 |
| JP | 11-512954 | 11/1999 |
| JP | 2001-507593 | 6/2001 |
| JP | 2001-513394 | 9/2001 |
| JP | 2003-509120 | 3/2003 |
| JP | 2003-204983 | 7/2003 |
| JP | 2003-334211 | 11/2003 |
| JP | 2004-208978 | 7/2004 |
| JP | 2004-306560 | 11/2004 |
| JP | 2004-330573 | 11/2004 |
| JP | 2005-87719 | 4/2005 |
| JP | 2005-219313 | 8/2005 |
| WO | WO 98/29063 | 7/1998 |
| WO | WO 03/096942 | 11/2003 |
| WO | WO 03/097764 | 11/2003 |

OTHER PUBLICATIONS

U.S. Appl. No. 10/450,521, filed Jun. 19, 2003, Usui et al.
U.S. Appl. No. 10/451,634, filed Jul. 9, 2003, Usui et al.
U.S. Appl. No. 10/386,723, filed Mar. 13, 2003, Usui.
U.S. Appl. No. 10/475,513, filed Oct. 27, 2003, Usui et al.
U.S. Appl. No. 10/524,211, filed Feb. 10, 2005, Usui et al.

* cited by examiner

HEAT GENERATING BODY, HEAT INSULATING METHOD USING THE SAME AND PACKAGING MATERIAL FOR DIE MOLDING HEAT GENERATION

This application is being cross referenced with the following fifteen applications filed on even date herewith:

| Inventors | Title | Int'l Appln No. |
|---|---|---|
| DODO, Toshihiro | PROCESS FOR PRODUCING HEAT GENERATING MIXTURE, HEAT GENERATING MIXTURE, HEAT GENERATING COMPOSITION, AND HEAT GENERATING BODY | PCT/JP05/012998 |
| DODO, Toshihiro | ACTIVE IRON POWDER, HEAT GENERATING COMPOSITION, AND HEAT GENERATING | PCT/JP05/012999 |
| DODO, Toshihiro | ACTIVE IRON POWDER AND HEAT GENERATING BODY | PCT/JP05/013000 |
| DODO, Toshihiro | HEAT GENERATING COMPOSITION, HEAT GENERATING BODY, AND PROCESS FOR PRODUCING HEAT GENERATING BODY | PCT/JP05/013001 |
| DODO, Toshihiro | WETTABLE HEAT GENERATING COMPOSITION COMPRESSED BODY, HEAT GENERATING BODY, AND PROCESS FOR PRODUCING WETTABLE HEAT GENERATING COMPOSITION COMPRESSED BODY | PCT/JP05/013002 |
| DODO, Toshihiro | HEAT GENERATING BODY AND PROCESS FOR PRODUCING HEAT GENERATING BODY | PCT/JP05/013003 |
| DODO, Toshihiro | HEAT GENERATING BODY AND PROCESS FOR PRODUCING THE SAME | PCT/JP05/013004 |
| DODO, Toshihiro | HEAT GENERATING BODY | PCT/JP05/013005 |
| DODO, Toshihiro | MICROHEATER AND PROCESS FOR PRODUCING THE SAME | PCT/JP05/013006 |
| DODO, Toshihiro | HEAT CLOTH AND PROCESS FOR PRODUCING THE SAME | PCT/JP05/013007 |
| DODO, Toshihiro | HEAT GENERATING PAD AND METHOD OF USE OF THE SAME | PCT/JP05/013008 |
| DODO, Toshihiro | HEAT GENERATING BODY | PCT/JP05/013009 |
| DODO, Toshihiro, et al. | FOOT WARMING HEAT GENERATING BODY AND PROCESS FOR PRODUCING FOOT WARMING HEAT GENERATING BODY | PCT/JP05/013011 |
| DODO, Toshihiro | HEAT GENERATING BODY | PCT/JP05/013015 |
| DODO, Toshihiro | FLEXIBLE HEAT GENERATING BODY | PCT/JP05/013017 |

TECHNICAL FIELD

The present invention relates to an irregular heat generating body having an integral structure of at least one continuous layer made of a raw material which is flexible and which when heated, is less in a change of the flexibility and having two or more plural sectional exothermic parts as provided at intervals by a sectioned part which is a heat seal part within the integral structure. In detail, the invention relates to a heat generating body in which a heat generating composition molded body present in the sectional exothermic part causes heat generation upon permeation of oxygen. In more detail, the invention relates to a heat generating body which is able to relax symptoms such as stiff shoulder, low-back pain, abdominal pain, joint pain, and muscular fatigue and which in particular, can be suitably used for relaxation of a symptom of menstrual pain, to a heat insulating method using the same and to a packaging material for die molding heat generation.

BACKGROUND ART

For the purpose of relaxing various symptoms such as menstrual pain, there have hitherto been used warm patch materials which upon sticking onto an affected part, expand a blood vessel to increase a blood flow, raise the temperature of the affected part and promote metabolism. Such a patch material is composed of a support and a sticky ointment layer containing a drug. With respect to an ejector of a drug, only a function for penetrating the drug into an affected part is emphasized. Accordingly, for the purposes of making the presence thereof thin during sticking to the skin, improving a sticking feeling to the skin and making it hard to be peeled away from the skin, a material which is flexible and stretchable is selected as the support.

Furthermore, examples of a heating pad include electrically heating pads and heat generating bodies utilizing an oxidation reaction of iron.

Heat generating compositions utilizing an oxidation reaction of a metal such as iron have been provided as a powder or granule, or a viscous material or creamy material. Heat generating bodies utilizing such a heat generating composition are very excellent in view of costs, safety, exothermic temperature, and so on and are already put into practical use as, for example, a so-called chemical body warmer as filled in an air-permeable bag.

In order to obtain a more comfortable feeling for use, there have been proposed various heat generating compositions which design to have shape holding properties and to hold exothermic characteristics while using a thickener, a binding agent, etc. in quest of prevention of deviation of a heat generating composition and fitness to various kinds of shapes.

For example, Patent Document 1 proposes a process for producing a heat generating composition as granulated so as to have an average particle size of 0.5 mm or more and a process for producing a heat generating composition having an improved granular strength by blending from 10 to 20 parts by weight of an adhesive binder component in addition water and granulating.

Also, Patent Document 2 proposes a throwaway body warmer composed of a heat generating composition having shape holding characteristics by adding a powdered thickener such as corn starch and potato starch.

Also, Patent Document 3 proposes a solid heat generating composition as prepared by mixing a binding agent such as CMC in a powdered or granular heat generating composition and compression molding the mixture.

Also, Patent Document 4 proposes a heat generating body as prepared by using a crosslinking agent, etc. and a water absorptive polymer and integrating them under pressure.

Also, Patent Document 5 proposes a heat generating composition in an ink form and/or a creamy form using a thickener so as to have viscosity, a heat generating body and a process for producing the same.

Also, Patent Document 6 proposes a heat generating composition molded body using a binding agent, the surface of which is covered by an air-permeable film material such as CMC, thereby designing to hold the shape.

Also, Patent Document 7 and Patent Document 8 each proposes a heat generating composition as processed into a viscous material or a creamy material, in which the shape is changed from a conventional rectangle to a foot shape or an elliptical shape so as to adapt to the outline of a body to be warmed.

Also, Patent Document 9 and Patent Document 10 each discloses a heat generating body in which a powdered heat generating composition is filled in sectioned divisions and which is made of plural exothermic parts as divided by a seal part.

Also, Patent Document 11, Patent Document 12, Patent Document 13, Patent Document 14, Patent Document 15 and Patent Document 16 each proposes a heat generating composition using a flocculant and a dry binding agent and a heat generating body in which a heat generating composition exothermic part is sectioned into plural divisions by using a substrate having an accommodating pocket.

Also, it is said that a symptom of menstrual pain is caused when a direct stimulus in the affected part or an indirect stimulus which has passed from the central nerve through the peripheral nerve due to a mental stimulus causes tension of a muscle or tendon, whereby vital energy and blood stay in the affected part. Accordingly, in order to relax a symptom of menstrual pain, it is said that it is effective to relieve the tension of a muscle or tendon which hinders the flow of vital energy and blood.

Also, in order to relax a symptom of poor circulation, it is said that it is effective to warm an area beneath the navel.

In order to dissolve the foregoing problems, there has been proposed an electrically heating pad. Though the electrically heating pad is excellent in adjusting capability of the temperature for compensating clothes of a user, the device becomes large in size and complicated so that it is problematic in portable use.

Also, in conventional heat generating bodies utilizing an oxidation reaction of iron, an exothermic part is large so that warming along the muscular or tendon direction was not obtainable.

Also, in a heat generating body utilizing an oxidation reaction of iron and provided with an opening as an oxygen-permeable measure, a chemical substance for heat generation which is a heat generating composition uses a flocculant aid, a flocculant, a dry binding agent, an agglomeration aid, and the like and is compressed and shaped, whereby the chemical substance for heat generation is prevented from leakage from the opening by perforation. The exothermic performance of the chemical substance for heat generation becomes worse thereby, and therefore, the heat generation body which withstands for practical use becomes inevitably large in size.

Also, in the case of using a chemical substance for heat generation which does not contain a flocculant aid, a flocculant, a dry binding agent, an agglomeration aid, and the like, it is necessary to previously prepare an accommodating pocket in an accommodating packaging material. In cells for heat generation and heat generating bodies having cells for heat generation embedded therein, there was involved a problem that their production becomes complicated.

[Patent Document 1] JP-A-4-293989
[Patent Document 2] JP-A-6-343658
[Patent Document 3] JP-A-59-189183
[Patent Document 4] WO 00/13626
[Patent Document 5] JP-A-9-75388
[Patent Document 6] JP-A-60-101448
[Patent Document 7] JP-A-9-276317
[Patent Document 8] JP-A-11-299817
[Patent Document 9] JP-A-1-110718
[Patent Document 10] JP-UM-A-6-26829
[Patent Document 11] JP-A-2000-288008
[Patent Document 12] JP-T-11-507593
[Patent Document 13] JP-T-11-508314
[Patent Document 14] JP-T-11-508786
[Patent Document 15] JP-T-11-512954
[Patent Document 16] JP-T-2002-514104

DISCLOSURE OF THE INVENTION

Problems that the Invention is to Solve

In view of the foregoing, an object of the invention is to provide a heat generating body which is able to relax symptoms such as stiff shoulder, low-back pain, muscular fatigue, menstrual pain, a symptom of poor circulation and in particular, can be suitably used for relaxation of a symptom of menstrual pain.

Means for Solving the Problems

Then, in order to solve the foregoing problems of the related art, the present inventor made extensive and intensive investigations and carried out various systematic experiments. As a result, he has reached the invention.

Specifically, as set forth in claim 1, a heat generating body of the invention is a heat generating body wherein a heat generating composition molded body resulting from molding a moldable heat generating composition containing surplus water as a connecting substance is interposed between packaging materials and the periphery of the heat generating composition molded body is heat sealed, which is characterized in that:

1) the packaging materials are each constituted of a substrate and a covering material, 2) the substrate is substantially planar and does not have an accommodating pocket, 3) the packaging material has a bending resistance of not more than 100 mm, 4) the packaging materials are each a non-elastic body at least at a temperature between 25° C. and 60° C., has a breaking strength of 500 g/mm$^2$ or more at 25° C. and has a breaking elongation of 30% or more at 90° C., 5) the moldable heat generating composition contains, as essential components, an iron powder, a carbon component, a reaction accelerator and water, has a water content of from 1 to 60% by weight, does not contain a flocculant aid, a flocculant, an agglomeration aid, a dry binder, a dry binding agent, a dry binding material, a sticky raw material, a thickener and an excipient, contains the surplus water so as to have a water mobility value of from 0.01 to 20, has moldability due to the surplus water, with the water in the moldable heat generating composition not functioning as a barrier layer, and is capable of causing an exothermic reaction upon contact with air, 6) plural sectional exothermic parts as divided by a sectioned part which is formed by heat sealing are provided, 7) the heat generating body contains a region having a ratio of bending resistance in the orthogonal directions of 2 or more on the surface thereof orthogonal to the thickness direction of the heat generating body, 8) at least a part of the heat generating body has permeability to air, and 9) the heat generating body has a fixing measure on at least a part of the exposed surface thereof.

Also, a heat generating body as set forth in claim 2 is characterized in that in the heat generating body as set forth in claim 1, the packaging materials are each constituted of a laminate of a fibrous material and a film-like material; and a raw material of each of the fibrous material and the film-like material is a material made of polyethylene inclusive of one as produced using a metallocene catalyst, polypropylene, a nylon, a polyester, polyvinyl chloride, polyvinylidene chloride, polyurethane, polystyrene, a saponified ethylene-vinyl acetate copolymer, an ethylene-vinyl acetate copolymer, a natural rubber, a regenerated rubber, a synthetic rubber, or a mixture thereof.

Also, a heat generating body as set forth in claim 3 is characterized in that in the heat generating body as set forth in claim 2, the fibrous material is a non-woven fabric; the film-like material is a polyethylene-made porous film; and the non-woven fabric and the polyethylene-made porous film are laminated via an air-permeable sticky layer.

Also, a heat generating body as set forth in claim 4 is characterized in that in the heat generating body as set forth in claim 1, the substrate or the covering material is non-shrinkable at 90° C.

Also, a heat generating body as set forth in claim 5 is characterized in that in the heat generating body as set forth in claim 1, the packaging materials each has a breaking elongation of 100% or more at 90° C.

Also, a heat generating body as set forth in claim 6 is characterized in that in the heat generating body as set forth in claim 1, the heat generating composition contains at least one member selected from additional components consisting of a water retaining agent, a water absorptive polymer, a pH adjusting agent, a hydrogen formation inhibitor, an aggregate, a fibrous material, a functional substance, a surfactant, an organosilicon compound, a pyroelectric substance, a moisturizer, a fertilizer component, a hydrophobic polymer compound, a heat generating aid, a metal other than iron, a metal oxide other than iron oxide, an acidic substance, and a mixture thereof.

Also, a heat generating wrap as set forth in claim 7 is characterized in that in the heat generating body as set forth in claim 1, the heat seal part is heat sealed after temporary adhesion by an adhesive layer; and an adhesive component which constitutes the adhesive layer and a component of a heat sealing material which constitutes the heat seal layer are copresent in the heat seal part.

As set forth in claim 8, a heat warming method of the invention is characterized by putting the heat generating body as set forth in any one of claims 1 to 10 on a necessary part of the body and keeping the skin temperature at from 32 to 50° C. for from 20 seconds to 24 hours.

Also, a heat insulating method as set forth in claim 9 is characterized in that in the heat warming method as set forth in claim 8, the temperature to be kept is from 32 to 39° C.

As set forth in claim 13, a packaging material for die molding heat generation of the invention is a packaging material which is used in the heat generating body as set forth in claim 1, which is characterized in that the packaging material is a non-elastic body at least at a temperature between 25° C. and 60° C., has a breaking strength of 500 g/mm$^2$ or more at 25° C. and has a breaking elongation of 30% or more at 90° C. and is made of a thermoplastic resin-made fibrous material and a thermoplastic resin-made film-like material.

Also, in the heat generating body, it is preferable that the heat generating composition molded body has a maximum height of from 0.1 to 10 mm; and that the sectioned part has a width of from 0.3 to 50 mm.

Also, in the heat generating body, it is preferable that the heat generating composition molded body and the sectional exothermic parts have a disc-like shape; that the disc has a diameter of from 1 to 50 mm and a maximum height of from 0.1 cm to 10 mm; and when the heat generating composition molded body is sealed in the sectional exothermic parts, a ratio of the capacity of the sectional exothermic parts to the volume of the heat generating composition molded body is from 0.6 to 1.0.

Also, in the heat generating body, it is preferable that the fixing measure is an adhesive layer; and that the adhesive layer contains at least one member selected from additional components consisting of a water retaining agent, a water absorptive polymer, a pH adjusting agent, a surfactant, an organosilicon compound, a hydrophobic polymer compound, a pyroelectric substance, an antioxidant, an aggregate, a fibrous material, a moisturizer, a functional substance, and a mixture thereof.

Advantages of the Invention

By the foregoing constitution, the heat generating body of the invention has the following advantages.

That is, the heat generating body of the invention is an integral heat generating body which is produced directly from a moldable heat generating composition, a substrate and a covering material but not by previously preparing an exothermic part and embedding it in a packaging material. By constituting the exothermic part from sectional exothermic parts and a sectioned part along the same, it is regulated that on the surface orthogonal to the thickness direction of the heat generating body, with respect to bending resistances in one direction and the direction orthogonal thereto, a ratio of bending resistance is 2 or more and that a minimum bending resistance in one direction on the surface orthogonal to the thickness direction of the heat generating body is not more than 100 mm. Thus, the fitness to an adherend and handling properties have been remarkably improved.

Then, it is possible to relax symptoms such as stiff shoulder, low-back pain, joint pain, muscular pain, and menstrual pain. Especially, it can be effectively used for relaxation of a symptom of menstrual pain.

Also, by using a laminate of a fibrous material and a film-like material, when a heat generating composition molded body is laminated on a substantially planar substrate and a covering material is put thereon, followed by heat sealing, it has become possible to prepare a heat generating body by one stage and to achieve an improvement of the production speed and a reduction of the costs.

Also, by using a laminate of a fibrous material and a film-like material, it is possible to efficiently produce a heat generating body in which sectional exothermic parts containing a heat generating composition molded body are provided at intervals via a sectioned part. On the surface orthogonal to the thickness direction of the heat generating body, since a region having a ratio of bending resistance of 2 or more is contained in at least a part of the heat generating body, it is possible to easily fix the heat generating body such that it follows along the curved surface of the body, etc.

Also, since the bending resistance in one direction of the heat generating body having sectional exothermic parts is low, it is possible to easily wind up the heat generating body in that direction, to compactly accommodate and store it in an outer bag which is an air-impermeable accommodating bag for storage and to relieve the deterioration of a heat generating composition.

BEST MODES FOR CARRYING OUT THE INVENTION

The invention is concerned with a heat generating body wherein a heat generating composition molded body resulting from molding a moldable heat generating composition containing surplus water as a connecting substance is interposed between packaging materials and the periphery of the heat generating composition molded body is heat sealed, which is characterized in that:

1) the packaging materials are each constituted of a substrate and a covering material,
2) the substrate is substantially planar and does not have an accommodating pocket,
3) the packaging materials each has a bending resistance of not more than 100 mm,
4) the packaging materials are each a non-elastic body at least at a temperature between 25° C. and 60° C., has a breaking strength of 500 g/mm$^2$ or more at 25° C. and has a breaking elongation of 30% or more at 90° C.,
5) the moldable heat generating composition contains, as essential components, an iron powder, a carbon component, a reaction accelerator and water, has a water content of from 1 to 60% by weight, does not contain a flocculant aid, a flocculant, an agglomeration aid, a dry binder, a dry binding agent, a dry binding material, a sticky raw material, a thickener and an excipient, contains the surplus water so as to have a water mobility value of from 0.01 to 20, has moldability due to the surplus water, with the water in the moldable heat generating composition not functioning as a barrier layer, and is capable of causing an exothermic reaction upon contact with air,
6) plural sectional exothermic parts as divided by a sectioned part which is formed by heat sealing are provided,
7) the heat generating body contains a region having a ratio of bending resistance in the orthogonal directions of 2 or more on the surface thereof orthogonal to the thickness direction of the heat generating body,
8) at least a part of the heat generating body has permeability to air, and
9) the heat generating body has a fixing measure on at least a part of the exposed surface thereof.

By the foregoing constitution, since the packaging materials which are less in a change of the temperature for use are used, a dimensional change due to the packaging material is less at the time of use, and the structural flexibility due to the bending resistance is kept. Thus, stable and adequate flexibility is kept in the heat generating body.

Furthermore, at least one of the packaging materials which are used is a packaging material having a breaking elongation of 30% or more at 90° C. (usually the covering material). Accordingly, in the case of putting a substantially planar covering material on a heat generating composition molded body as laminated on a substantially planar substrate and heat sealing the periphery of the heat generating composition molded body, wrinkles which cause seal leakage are not generated so that a seal part which is free from seal cut can be formed. Incidentally, the covering material may partially have a concave. Furthermore, by using a packaging material which is non-stretchable at 90° C. for the substrate or the covering material, it is possible to prevent the generation of wrinkles in the heat generating body from occurring.

Furthermore, by using a packaging material which is non-stretchable at 90° C. for at least one of the substrate or the covering material, the generation of wrinkles of the heat generating body is prevented from occurring. In this way, the heat generating body having a ratio of bending resistance of 2 or more has both flexibility and rigidity.

Furthermore, by combining sectional exothermic parts with a sectioned part, the heat generating body of the invention can adapt to the body. Furthermore, since the heat generating body of the invention has an installation measure, it can be provided with morphology and effective heat transfer properties. Thus, it is possible to provide effective relaxation and remedy using the heat generating body.

Furthermore, by adjusting the size and interval of the convex sectional exothermic parts of the heat generating body of the invention, an exothermic part which is flexible and exhibits uniform temperature distribution or an exothermic part which exhibits pattern-like temperature distribution is obtained. By the pattern-like temperature distribution, it is possible to improve an acupuncture point effect of the warming part.

Furthermore, by using a raw material having a bending resistance of not more than 100 mm, preferably not more than 60 mm, more preferably from 10 to 60 mm, and further preferably from 10 to 50 mm for the substrate or the covering material, a positive impression is obtained at the time of contact with the body or at the time of use.

Since the heat generating body of the invention is made of sectional exothermic parts containing a heat generating composition molded body, a sectioned part not containing a heat generating composition molded body and an installation measure and the heat generating composition molded body is substantially densely sealed in each of the sectional exothermic parts, the sectional exothermic part does not easily warp. On the other hand, since the sectioned part is a heat seal part, does not contain a heat generating composition molded body and is made of a raw material having a bending resistance of not more than 100 mm, the sectioned part easily warps and can be bent. The sectioned part works as a hinge at least at a temperature between 25° C. and 60° C. and can more easily adapt to the body of a user as a heat generating body than one made of a single exothermic part.

Furthermore, each of the packaging materials is a non-elastic body at least under the circumference between 25° C. and 60° C., has a breaking strength of 500 g/mm$^2$ or more at 25° C. and has a breaking elongation of 30% or more at 90° C. Furthermore, in the heat generating body of the invention, at least one of the packaging materials is made of a heat sealable and flexible raw material which is a laminate of a fibrous material and a film-like material.

In the packaging materials, the sectional exothermic parts containing a heat generating composition molded body or a heat generating composition compressed body as a compressed body thereof have a high bending resistance, and the sectioned part present between the sectional exothermic parts, which does not contain a heat generating composition molded body or a heat generating composition compressed body (hereinafter referred to as "heat generating composition molded body) as a compressed body thereof and which is a heat seal part, has a low bending resistance. Since the exothermic part made of the sectional exothermic parts and the sectioned part can keep the bending resistance at a temperature between about 0° C. and about 80° C., the sectioned part functions as a hinge and is bent preferentially to the sectional exothermic parts. In the heat generating body made of sectional exothermic parts and a sectioned part, the sectioned part functions as a hinge at from the normal temperature to the time of heating (from about 23° C. to about 50° C.) and is bent preferentially to the sectional exothermic parts. At the time of heating, a good bending resistance difference is still kept. As a result, the heat generating body keeps structural supporting of the sectional exothermic parts and has sufficient rigidity during the production or use. On the other hand, even when heated, the heat generating body still keeps an excellent bending resistance.

In the heat generating body in which the foregoing packaging material is used for at least one of the substrate or the covering material, a heat generating composition molded body is laminated on a substantially planar substrate, a covering material is put thereon, and the periphery of the heat generating composition molded body is heat sealed, whereby a sectioned part which is a seal part is formed. As one example, in the case of using the foregoing packaging material as the covering material, since the covering material is flexible and non-elastic at least at a temperature between 25° C. and 60° C. and has a breaking strength of 500 g/mm$^2$ or more at 25° C., it warps but has nerve and is able to surely cover the heat generating composition molded body. In addition, at the time of heat sealing, since this covering material has a breaking elongation of 100% or more at 90° C., the covering material does not cause breakage due to the temperature at the time of heat sealing, is free from seal cut and is able to form a secure heat seal part. Accordingly, in the heat generating body of the invention having an exothermic part made of sectional exothermic parts containing a heat generating composition molded body and a sectioned part not containing a heat generating composition molded body, the sectional exothermic parts containing a heat generating composition molded body or a heat generating composition compressed body as a compressed body thereof have a high bending resistance, and the sectioned part present between the sectional exothermic parts, which does not contain a heat generating composition molded body or a heat generating composition compressed body as a compressed body thereof and which is a heat seal part, has a low bending resistance. Since the exothermic part made of the sectional exothermic parts and the sectioned part can keep the bending resistance at a temperature between about 0° C. and about 80° C., the sectioned part functions as a hinge and is bent preferentially to the sectional exothermic parts. In the heat generating body made of sectional exothermic parts and a sectioned part, the sectioned part functions as a hinge at from the normal temperature to the time of heating (from about 23° C. to about 50° C.) and is bent preferentially to the sectional exothermic parts. At the time of heating, a good bending resistance difference is still kept. As a result, the heat generating body keeps structural supporting of the sectional exothermic parts and has sufficient rigidity during the production or use. On the other hand, even when heated, the heat generating body still keeps an excellent bending resistance.

The heat generating body of the invention easily adapts to a wide range of the outline of the body and has a ratio of bending resistance of 2 or more while realizing sustaining, simple and comfortable warmth-taking and excellent adaptability to the body shape. Thus, it keeps sufficient rigidity for preventing taking-out of the contents of the sectional exothermic parts without generating a fold and/or a protuberance during the use.

In the heat generating body of the invention, the moldable heat generating composition is activated by oxygen which is obtained from the circumferential air, thereby causing heat generation. Since the covering material feeds oxygen in the sectional exothermic parts, it has permeability to air.

The plural sectional exothermic parts are disposed isolated from each other, and each sectional exothermic part functions independent from the remaining sectional exothermic parts. Since the heat generating composition molded body is densely packed in each of the sectional exothermic parts, by disposing the sectional exothermic parts at intervals, it is possible to make the heat generating body easily adapt to the outline of the body as compared with one made of a single exothermic part. The heat generating composition molded body may be compressed as a compressed body in each of the sectional exothermic parts. Therefore, the sectional exothermic parts are not easily bent, whereas the sectioned part between the sectional exothermic parts can be bent because a heat generating composition is not present therein. Thus, it is possible to reveal adaptability to the body.

It is preferable that the respective sectional exothermic parts have a similar amount of the heat generating composition molded body and similar oxygen permeability. Separately, so far as the temperature of the sectional exothermic parts as generated consequently is similar, the amount, shape and oxygen permeability of the heat generating composition may be different between the sectional exothermic part and the sectional exothermic part.

As described previously, the sectional exothermic parts of the invention do not have a structure in which an exothermic part as prepared from a certain packaging material and a heat generating composition is packaged by a substrate and a covering material each of which is a packaging material but has an integral structure in which a heat generating composition molded body resulting from molding a moldable heat generating composition is packaged by a substrate and a covering material and sealed.

A raw material of the substrate or covering material is not limited so far as it functions as an accommodating bag of the heat generating composition. Usually, raw materials which are used in chemical body warmers or heat generating bodies can be used. Examples of the raw material include air-impermeable raw materials, air-permeable raw materials, water absorptive raw materials, non-water absorptive raw materials, non-extensible raw materials, extensible raw materials, stretchable raw materials, non-stretchable raw materials, foamed raw materials, non-foamed raw materials, non-heat sealable raw materials, and heat sealable raw materials. The raw material can be properly used depending upon a desired utility in a desired form such as films, sheets, non-woven fabrics, woven fabrics, and composites thereof.

In general, the substrate is made of an air-impermeable film or sheet, and the covering material is made of an air-permeable film or sheet or non-woven fabric, and vice versa. The both may be air-permeable. As the underlay material, an air-permeable underlay material and an air-impermeable underlay material may be used for different purposes.

The packaging material of the accommodating bag may be of a single-layered structure or multilayered structure, and its structure is not limited. Furthermore, though the packaging material is composed of at least a substrate and a covering material, a packaging material for laminating the heat generating composition molded body is the substrate, and a packaging material for covering on the heat generating composition molded body is the covering material regardless of whether the packaging material is air-permeable or air-impermeable. An embodiment of a multilayered structure in which an air-impermeable packaging material is the substrate and an air-permeable packaging material is the covering material will be hereunder described as one example. That is, in this embodiment, the substrate is made of layer A/layer B, layer A/layer B/layer C, or layer A/layer B/layer C/layer D; and the covering material is made of layer F/layer G, layer E/layer F/layer G, or layer F/layer H/layer G. Examples of the layer A include thermoplastic resin films (for example, polyethylene), heat seal layers (for example, polyethylene and EVA), and water absorptive papers; examples of the layer B include non-woven fabrics of a thermoplastic resin (for example, nylons), non-water absorptive papers, water absorptive papers, thermoplastic resin films (for example, polyethylene films, polypropylene films, polyester films, and polyamide (for example, nylons) films), wicks (for example, non-water absorptive papers and water absorptive papers); examples of the layer C include adhesive layers, non-water absorptive papers, water absorptive papers, thermoplastic resin films (for example, polyethylene), non-slip layers, and non-woven fabrics of a thermoplastic resin (for example, polyesters and nylons); examples of the layer D include separators, thermoplastic resin films (for example, polyethylene), and non-woven fabrics; examples of the layer E include heat seal layers; examples of the layer F include porous films or perforated films made of a thermoplastic resin (for example, polyethylene), films made of a thermoplastic resin (for example, polyethylene), non-water absorptive papers, and water absorptive papers; examples of the layer G include non-woven fabrics of a thermoplastic resin (for example, polyesters and nylons); and examples of the layer H include non-water absorptive papers and water absorptive papers. Examples of the substrate or covering material include heat seal layer made of polyethylene obtained by using a metallocene catalyst/polypropylene film, polyethylene-made heat seal layer/polypropylene film, EVA-made heat seal layer/polypropylene film, EVA-made heat seal layer/polypropylene film/adhesive layer/separator, EVA-made heat seal layer/polyethylene film/nylon non-woven fabric, non-woven fabric/porous film, heat seal layer made of polyethylene obtained by using a metallocene catalyst/polyethylene film/nylon non-woven fabric, heat seal layer made of polyethylene obtained by using a metallocene catalyst/polypropylene film/polypropylene non-woven fabric, non-woven fabric/(paper and/or perforated (provided by a needle or laser) film)/porous film, non-woven fabric/(paper and/or porous film)/perforated (provided by a needle or laser) film, and non-woven fabric/(paper and/or porous film)/non-woven fabric. A method for laminating the respective layers is not limited. The respective layers may be directly laminated; the respective layers may be laminated via an air-permeable adhesive layer or a laminating agent layer; and the respective layers may be laminated by hot melt extrusion or the like. Furthermore, in the invention, it is to be noted that polyethylene produced by using a metallocene catalyst is also included in the polyethylene.

For example, in the case of laminating the foregoing raw material such as non-woven fabrics and porous films via an air-permeable sticky layer, examples of a method for forming the air-permeable sticky layer include a method in which a sticky substance is fibrillated by an appropriate system such as a curtain spray system, a melt blow system or a slot spray system for blowing and spreading a sticky substance via hot air under heat melting and spread and accumulated on an appropriate supporting substrate made of a porous film, an air-permeable substrate, a separator, etc., thereby forming a porous sticky layer.

A thickness of each of the substrate, the covering material, the underlay material, and the raw material constituting the same varies depending upon the utility and is not limited. The thickness is usually from 5 to 5,000 μm, preferably from 10 to 500 μm, and more preferably from 20 to 250 μm.

The air-impermeable raw material is not limited so far as it is air-impermeable. Examples thereof include films, sheets or coatings made of a polymer (for example, polyethylene, polypropylene, nylons, polyacrylates, polyesters, polyvinyl alcohols, and ethylene-vinyl acetate copolymers) and laminates thereof with a metal (including a semiconductor) compound (for example, silicon oxide) or composite raw materials using the same.

Of the foregoing air-impermeable raw materials, examples of a film having high air impermeability include films provided with a single layer or multiple layers of a thin film having a metal including a semiconductor or a compound thereof provided on an air-impermeable raw material film. Examples of the metal including a semiconductor include silicon, aluminum, and alloys or mixtures containing such a metal. Examples of the metal (including a semiconductor) compound include oxides, nitrides and oxynitrides of the foregoing metals or alloys or mixtures. Examples of the layer include silicon oxide layers, aluminum oxide layers, and silicon oxynitride layers; layers obtained by laminating an arbitrary layer of these layers on a polyester-made film; and layers obtained by further laminating a stretched polyolefin film (for example, a biaxially stretched polypropylene film) thereon.

The air-permeable raw material is not limited so far as it is air-permeable. Examples thereof include air-permeable films (for example, porous films and perforated films); materials having air permeability by themselves (for example, papers and non-woven fabrics); materials prepared by laminating at least one of papers and air-permeable films and non-woven fabrics so as to have air permeability; materials prepared by providing an air-impermeable packaging material comprising a non-woven fabric having a polyethylene film laminated thereon with fine pores by using a needle, etc. so as to have air permeability; non-woven fabric whose air permeability is controlled by laminating a fiber and heat bonding under pressure; porous films; and materials prepared by sticking a non-woven fabric onto a porous film. The "perforated film" as referred to herein is a film prepared by providing an air-impermeable film (for example, polyethylene films) with fine pores by using a needle so as to have air permeability.

The air permeability is not limited so far as the heat generation can be kept. In the case of use in usual heat generation, the air permeability is usually from 50 to 10,000 $g/m^2/24$ hr, preferably from 70 to 5,000 $g/m^2/24$ hr, more preferably from 100 to 2,000 $g/m^2/24$ hr, and further preferably from 100 to 700 $g/m^2/24$ hr in terms of moisture permeability by the Lyssy method.

When the moisture permeability is less 50 $g/m^2/24$ hr, the heat value is small and a sufficient thermal effect is not obtained, and therefore, such is not preferable. On the other hand, when it exceeds 10,000 $g/m^2/24$ hr, the exothermic temperature is high so that a problem in safety may possibly be generated, and therefore, such is not preferable. However, there is no limitation even when the moisture permeability exceeds 10,000 $g/m^2/24$ hr depending upon the utility, or even in the use at a moisture permeability closed to the open system, according to circumstances.

The stretchable packaging material is not particularly limited so far as it is stretchable. That is, it is only required that the stretchable packaging material is stretchable as a whole. The stretchable packaging material may be formed of a single material or a composite material of stretchable substrates or a combination of a stretchable substrate and a non-stretchable substrate.

Examples of the stretchable packaging material include single materials (for example, natural rubbers, regenerated rubbers, synthetic rubbers, elastomers, and stretchable shape memory polymers) and mixtures thereof, mixed materials or blended materials of such a stretchable raw material and a non-stretchable raw material or fabrics constituted of a combination of these materials, films, yarns, strands, ribbons, tapes, and stretchable films with a scrim structure.

The porous film is not limited and can be properly selected among porous films obtained by stretching a film made of a polyolefin based resin (for example, polyethylene, linear low density polyethylene, and polypropylene) or a fluorine based resin (for example, polytetrafluoroethylene) and a filler.

The non-woven fabric is not limited. Single non-woven fabrics of a single fiber or composite fiber made of a material such as rayon, nylons (polyamides), polyesters, polyacrylates, polypropylene, vinylon, polyethylene, polyurethane, cupra, cotton, cellulose, and pulp, or laminates of blended or accumulated fiber layers of such fibers are useful. Furthermore, from the standpoint of production process, dry non-woven fabrics, wet non-woven fabrics, spunbonds, spunlaces, and the like can be used. Non-woven fabrics made of a composite fiber having a core-sheath structure are also useful. A non-woven fabric in the side which is brought into contact with the skin is preferably a napping (fluffy) non-woven fabric. Also, stretchable non-woven fabrics and non-stretchable non-woven fabrics are useful.

The water absorptive raw material is not particularly limited so far as it is a water absorptive film or sheet.

The water absorptive raw material is not particularly limited so far as it has water absorption properties consequently regardless of whether or not the raw material has water absorption properties by itself.

Specific examples thereof include water absorptive foamed films or sheets having water absorption properties (for example, foamed bodies of water absorptive foamed polyurethane, etc.) or papers, non-woven fabrics or woven fabrics formed of a fiber having water absorption properties, non-woven fabrics or woven fabrics containing a fiber having water absorption properties, and water absorptive materials such as water absorptive porous films or sheets. Besides, there are enumerated materials in which regardless of the presence or absence of water absorption properties, a water absorbing agent is contained, impregnated, kneaded, transferred or carried on a foamed film or sheet, a non-woven fabric, a woven fabric or porous film or sheet, thereby imparting or increasing water absorption properties; and materials in which regardless of the presence or absence of water absorption properties, a water absorptive raw material such as water absorptive foamed films or sheets, papers, non-woven fabrics, woven fabrics, and porous films or sheets as cut in a planar shape according to the invention is attached to one side or both sides of the material according to the invention, thereby imparting water absorption properties.

In particular, in the heat generating body of the invention, for the purpose of forming the plane which is brought into contact with the skin into a comfortable plane by imparting water absorption properties against sweat, etc., in order that in the case of sweating, the sweat is absorbed, it is preferable that a packaging material in the plane which is brought into contact with the skin is constituted of a packaging material using a non-woven fabric or a woven fabric containing, as the major component, a water absorptive fiber having a water retention of 20% or more. Examples of the water absorptive fiber having a water retention of 20% or more include cottons, silks, hemps, wools, polyacrylonitrile based synthetic fibers, polyamide based synthetic fibers, polyvinyl alcohol based synthetic fibers, acetate fibers, triacetate fibers, and regenerated fibers. In addition, non-woven fabrics having a highly water absorptive polymer held in a non-woven fabric can be used as the non-woven fabric having excellent water absorption properties. Incidentally, non-woven fabrics or woven fabrics containing such a fiber as the major component are relatively good with respect to the feeling against the skin.

In addition, highly water absorptive packaging materials having high absorption properties of sweat can be used as the packaging material. Examples thereof include non-woven fabrics containing a fiber whose surface is coated with a highly water absorptive resin, non-woven fabrics containing a hollow fiber having a number of fine pores on the surface thereof, and non-woven fabrics containing a fiber having a capillary action by forming a number of pouches or plural layers in the cross-sectional shape.

Besides, non-woven fabrics or films having a water absorptive inorganic compound held on a non-sticky surface of a packaging material can be used. Examples thereof include non-woven fabrics resulting from holding a powder (for example, diatomaceous earth, zeolite, and silica gel) on a non-woven fabric and films resulting from holding a relatively large amount of a powder (for example, silica and alumina) on a synthetic resin (for example, polyethylene).

The fixing means is not limited so far as it has capability for fixing a thermal packaging body for joint surroundings or a material having an exothermic part to a prescribed part.

As the fixing means, an adhesive layer, a hook and eye, a hook and button, a hook and loop fastener such as Velcro, a magnet, a band, a string, and combination thereof can be arbitrarily used.

Incidentally, in the case of a band, fixing means for adjustment may be further constructed by a combination of a hook and loop fastener and an adhesive layer.

Here, the "hook and loop fastener" as referred to herein has a fastening function by a combination of a loop as a female fastener with a male fastener capable of fastening the female fastener thereto, which is known as trade names such as Magic Tape (a registered trademark), Magic Fastener (a registered trademark), Velcro Fastener, and Hook and Loop Tape. Examples of the material having a loop function include non-woven fabrics and woven fabrics of napped or hole-containing yarns. Such a material having a loop function (female fastener function) may be covered on the surface of a paddling forming the band, or the band may be constructed of such a material itself. Although the hook member which is the male fastener member is not particularly limited, examples thereof include hook members formed of a polyolefin based resin (for example, polyethylene and polypropylene), a polyamide, a polyester, etc. Although the shape of the hook is not particularly limited, a hook having a cross-sectional shape such as an I type, an inverted L type, an inverted J type, and a so-called mushroom type is preferable because it is easily hooked by the loop and does not give an extreme stimulus to the skin. Incidentally, the hook may be adhered to the entire area of a fastening tape, and only the hook may be used as a fastening tape while omitting a tape substrate.

The adhesive layer may contain at least one member selected from additional components consisting of a water retaining agent, a water absorptive polymer, a pH adjusting agent, a surfactant, an organosilicon compound, a hydrophobic polymer compound, a pyroelectric substance, an antioxidant, an aggregate, a fibrous material, a moisturizer, a functional substance, and a mixture thereof.

The adhesive of the invention is classified into a non-hydrophilic adhesive, a mixed adhesive, and a hydrophilic adhesive (for example, a gel).

The adhesive constituting the adhesive layer is not limited so far as it has an adhesive strength necessary for adhering to the skin or clothes. Adhesives of every form such as a solvent based adhesive, an aqueous adhesive, an emulsion type adhesive, a hot melt type adhesive, a reactive adhesive, a pressure-sensitive adhesive, a non-hydrophilic adhesive, and a hydrophilic adhesive are employable.

The adhesive layer includes one layer of a non-hydrophilic adhesive constituted of the non-hydrophilic adhesive and non-hydrophilic adhesive layers constituted of the non-hydrophilic adhesive.

It is to be noted that a material whose water absorption properties are improving by containing a water absorptive polymer or a water retaining agent in the non-hydrophilic adhesive layer is dealt as the non-hydrophilic adhesive layer.

A hot melt based adhesive may be provided between the hydrophilic adhesive layer and a substrate or a covering material.

Furthermore, in the case where the hydrophilic adhesive is provided in a thermal packaging body for joint surroundings, there is no limitation. After seal treating a thermal packaging body for joint surroundings, a hydrophilic adhesive layer may be provided in the thermal packaging body for joint surroundings.

Furthermore, the adhesive layer may or may not have air permeability and may be properly selected depending upon the utility. With respect to the air permeability, the adhesive layer may be air-permeable as a whole. Examples thereof include an adhesive layer having air permeability as a whole of a region in which an adhesive is partially present and a portion where no adhesive is present is partially present.

In laminating an adhesive on an air-permeable substrate and/or a covering material in a stratiform state as it is, examples of a method for keeping its air permeability include a method in which an adhesive layer is partially laminated by printing or transferring an adhesive, thereby forming a non-laminated part as an air-permeable part; a method in which an adhesive is transferred in one direction while drawing a circle in a filament-like form or properly moved in the two-dimensional directions by transferring in a zigzag manner, whereby a space of the filament-like adhesive keeps air permeability or moisture permeability or the adhesive is foamed; and a method for forming a layer by a melt blow system.

Examples of the adhesive which constitutes the non-hydrophilic adhesive layer include acrylic adhesives, polyvinyl acetate based adhesives (for example, vinyl acetate resin based emulsions and ethylene-vinyl acetate resin based holt melt adhesives), polyvinyl alcohol based adhesives, polyvinyl acetal based adhesives, vinyl chloride based adhesives, polyamide based adhesives, polyethylene based adhesives, cellulose based adhesives, chloroprene (neoprene) based adhesives, nitrile rubber based adhesives, polysulfide based adhesives, butyl rubber based adhesives, silicone rubber based adhesives, styrene based adhesives (for example, styrene based hot melt adhesives), rubber based adhesives, and silicone based adhesives. Of these, rubber based adhesives, acrylic adhesives, and adhesives containing a hot melt based polymer substance for the reasons that they are high in the adhesive strength, are cheap, are good in long-term stability, and are small in reduction of the adhesive strength even by providing heat.

In addition to the base polymer, if desired, the adhesive may be compounded with other components such as tackifiers (for example, petroleum resins represented by rosins, chroman-indene resins, hydrogenated petroleum resins, maleic anhydride-modified rosins, rosin derivatives, and C-5 based petroleum resins), phenol based tackifiers (especially, tackifiers having an aniline point of not higher than 50° C.; for example, terpene phenol based resins, rosin phenol based resins, and alkylphenol based resins), softeners (for example, coconut oil, castor oil, olive oil, camellia oil, and liquid paraffin), softeners, anti-aging agents, fillers, aggregates, adhesion adjusting agents, adhesion modifiers, coloring agents, anti-foaming agents, thickeners, and modifiers, thereby improving performance such as an improvement in adhesion to nylon-made clothes and mixed yarn clothes.

Examples of the hot melt based adhesive include known hot melt based adhesives imparted with adhesion. Specific examples thereof include styrene based adhesives made of, as a base polymer, an A-B-A type block copolymer (for example, SIS, SBS, SEBS, and SIPS), vinyl chloride based adhesives made of, as a base polymer, a vinyl chloride resin, polyester based adhesives made of, as a base polymer, a polyester, polyamide based adhesives made of, as a base polymer, a polyamide, acrylic adhesives made of, as a base polymer, an acrylic resin, polyolefin based adhesives made of, as a base polymer, a polyolefin (for example, polyethylene, super low density polyethylene, polypropylene, ethylene-α-olefin copolymers, and ethylene-vinyl acetate copolymers), 1,2-polybutadiene based adhesives made of, as a base polymer, 1,2-polybutadiene, and polyurethane based adhesives made of, as a base polymer, polyurethane; adhesives made of a modified body of the foregoing adhesive whose adhesion is improved or whose stability is changed; and mixtures of two or more kinds of these adhesives. Adhesive layers constituted of a foamed adhesive and adhesive layers constituted of a crosslinked adhesive can also be employed.

The non-aromatic hot melt based adhesive is not limited so far as it is made of, as a base polymer, a hot melt based adhesive not containing an aromatic ring. Examples thereof include olefin based hot melt based adhesives and acrylic hot melt based adhesives. As the non-aromatic polymer which is the base polymer not containing an aromatic ring, there are enumerated polymers or copolymers of an olefin or a diene. Examples thereof include olefin polymers. The olefin polymer includes polymers or copolymers of ethylene or an α-olefin. Also, polymers resulting from adding a diene (for example, butadiene and isoprene) as other monomer thereto may be employed.

The α-olefin is not limited so far as it is a monomer having a double bond in the terminal thereof. Examples thereof include propylene, butene, heptane, hexene, and octene.

The "aromatic hot melt based adhesive" as referred to herein is a hot melt based adhesive whose base polymer contains an aromatic ring. Examples thereof include styrene based hot melt based adhesives represented by A-B-A type block copolymers.

In the foregoing A-B-A type block copolymers, the A block is a non-elastic polymer block made of a monovinyl substituted aromatic compound A such as styrene and methylstyrene; and the B block is an elastic polymer block made of a conjugated diene such as butadiene and isoprene. Specific examples thereof include a styrene-butadiene-styrene block copolymer (SBS), a styrene-isoprene-styrene block copolymer (SIS), and hydrogenated types thereof (for example, SEBS and SIPS), and mixtures thereof.

As a countermeasure for preventing a lowering of adhesive strength caused due to an increase of water of the non-hydrophilic adhesive layer, an adhesive layer obtained by further compounding a water absorptive polymer in the non-hydrophilic adhesive can be used.

The hydrophilic adhesive which constitutes the hydrophilic adhesive layer is not particularly limited so far as it contains a hydrophilic polymer or a water-soluble polymer as the major component, has adhesion and is hydrophilic as an adhesive.

Examples of the constitutional components of the hydrophilic adhesive include hydrophilic polymers (for example, polyacrylic acid), water-soluble polymers (for example, poly (sodium acrylate) and polyvinylpyrrolidone), crosslinking agents (for example, dry aluminum hydroxide and meta-silicic acid aluminic acid metal salts), softeners (for example, glycerin and propylene glycol), higher hydrocarbons (for example, soft liquid paraffin and polybutene), primary alcohol fatty acid esters (for example, isopropyl myristate), silicon-containing compounds (for example, silicone oil), fatty acid glycerin esters (for example monoglycerides), oily components (for example, vegetable oils such as olive oil), antiseptics (for example, methyl p-hydroxybenzoate and propyl p-hydroxybenzoate), solubilizing agents (for example, N-methyl-2-pyrrolidone), thickeners (for example, carboxymethyl cellulose), surfactants (for example, polyoxyethylene hardened castor oil and sorbitan fatty acid esters), hydroxycarboxylic acid (for example, tartaric acid), excipients (for example, light silicic anhydride, water absorptive polymers, and kaolin), moisturizers (for example, D-sorbitol), stabilizers (for example, sodium edetate, p-hydroxybenzoic acid esters, and tartaric acid), crosslinking type water absorptive polymers, boron compounds (for example, boric acid), and water. They may be used as an arbitrary combination.

A temporary adhering seal part is formed via a sticky layer. An adhesive which constitutes the sticky layer is a layer formed of a polymer composition which is tacky at the normal temperature and is not limited so far as it can be heat sealed after temporary adhesion.

Furthermore, the foregoing adhesives of the sticky layer can be used as the adhesive which constitutes the sticky layer as used for temporary adhesion. Of these, non-hydrophilic adhesives are preferable. With respect to the adhesive constituting the adhesive layer, it is preferable that the adhesive is well compatible with a heat seal material constituting a heat seal and that a melting point of the base polymer of the adhesive is not higher than a melting point of the heat seal material. Hot melt based adhesives are especially preferable for hot melt based bonding agents. Furthermore, in the case where the heat seal material is an olefin based raw material, preferred examples thereof include olefin based adhesives.

A bonding layer for fixing the air permeability adjusting material is constituted of a bonding agent or an adhesive which is usually used. In particular, an adhesive is useful, and the foregoing adhesives for constituting the adhesive layer can be used.

Furthermore, a method for providing a bonding layer is not limited so far as the air permeability adjusting material can be fixed. The bonding layer may be entirely provided or partially or intermittently provided. Examples of its shape include various shapes such as a network-like shape, a stripe-like shape, a dot-like shape, and strip-like shape.

Furthermore, in the case where an adhesive layer is employed as the hydrophilic adhesive layer, if there is a difference in a water retaining force between the hydrophilic adhesive layer and the heat generating composition molded body, transfer of water occurs via a packaging material present therebetween such as a substrate, thereby causing in-conveniences against the both. In particular, the transfer of water occurs during the storage. In order to prevent this, it is preferable that the packaging material present therebetween at least has a moisture permeability of not more than 2 $g/m^2$/day in terms of a moisture permeability according to the Lyssy method. By using this, in the case where the heat generating body is accommodated in an outer bag as an air-impermeable accommodating bag and stored, the transfer of water can be prevented.

In the case where a hydrophilic adhesive layer is used as the adhesive layer, the moisture permeability of a moisture-proof packaging material provided between the heat generating composition molded body and the hydrophilic adhesive layer is not limited so far as the transfer of water can be prevented within the range where the exothermic performance is not affected. The moisture permeability according to the Lyssy method is usually not more than 2 $g/m^2$/day, preferably not more than 1.0 $g/m^2$/day, more preferably not more than 0.5 $g/m^2$/day, and further preferably from 0.01 to 0.5 $g/m^2$/day. These values are a value under a condition under an atmospheric pressure at 40° C. and 90% RH. Incidentally, the moisture-proof packaging material can be used as a substrate or a covering material and may be laminated singly on a substrate, a covering material, or the like.

The moisture-proof packaging material is not limited so far as the transfer of water between the heat generating composition molded body and the hydrophilic adhesive layer can be prevented. Examples thereof include metal vapor deposited films, vapor deposited films of a metal oxide, metal foil-laminated films, EVOH (ethylene/vinyl alcohol copolymer or ethylene/vinyl acetate copolymer saponified product) based films, biaxially stretched polyvinyl alcohol films, polyvinylidene chloride coated films, polyvinylidene chloride coated films obtained by coating polyvinylidene chloride on a substrate film (for example, polypropylene), metal foils such as an aluminum foil, air-impermeable packaging materials obtained by vapor depositing or sputtering a metal (for example, aluminum) on a polyester film substrate, and packaging laminates using a transparent barrier film of a structure in which silicon oxide or aluminum oxide is provided on a flexible plastic substrate. The air-impermeable packaging materials which are used in the outer bag, etc. can also be used.

Furthermore, packaging materials such as moisture-proof packaging materials as described in JP-A-2002-200108, the disclosures of which can be incorporated herein by reference, can be used.

In the case of using a water-containing hydrophilic adhesive (for example, a gel) in the adhesive layer, in order to adjust the moisture equilibrium between the heat generating composition and the adhesive layer, the content of a reaction accelerator (for example, sodium chloride) or a substance having a water holding power (for example, a water absorptive polymer) in the heat generating composition may be adjusted within the range of from 10 to 40% by weight, preferably from 15 to 40% by weight, and more preferably from 15 to 30% by weight based on the heat generating composition.

Furthermore, as the adhesive having good moisture permeability and low stimulation to the skin, water-containing adhesives (for example, hydrophilic adhesives and gels) as described in JP-A-10-265373 and JP-A-9-87173, adhesives which can be subjected to hot melt coating as described in JP-A-6-145050 and JP-A-6-199660, and rubber based adhesives as described JP-A-10-279466 and JP-A-10-182408, the disclosures of which are totally incorporated herein by reference, are useful.

The functional substance which is contained in the adhesive layer is not limited so far as it is a substance having any function. There can be enumerated at least one member selected from aromatic compounds, vegetable extracts, crude drugs, perfumes, slimming agents, analgesics, blood circulation promoters, swelling improvers, antibacterial agents, sterilizers, mold inhibitors, odor eaters, deodorants, percutaneously absorptive drugs, fat-splitting components, minus ion generators, far infrared ray radiants, magnetic bodies, fomentations, cosmetics, bamboo vinegar, and wood vinegar.

Specific examples thereof include aromatic compounds (for example, menthol and benzaldehyde), vegetable extracts (for example, mugwort extract), crude drugs (for example, moxa), perfumes (for example, lavender and rosemary), slimming agents (for example, aminophylline and tea extract), analgesic drugs (for example, indomethacin and dl-camphor), blood circulation promoters (for example, acidic mucopolysaccharide and chamomile), swelling improvers (for example, horse chestnut extract and flavone derivatives), fomentations (for example, aqueous boric acid, physiological saline, and aqueous alcohols), fat-splitting components (for example, jujube extract, caffeine, and tonalin), cosmetics (for example, aloe extracts, vitamin preparations, hormone preparations, anti-histamines, and amino acids), antibacterial agents and sterilizers (for example, carbolic acid derivatives, boric acid, iodine preparations, invert soaps, salicylic acid based substances, sulfur, and antibiotics), and mold inhibitors.

The percutaneously absorptive drug is not particularly limited so far as it has percutaneous absorption. Examples thereof include corticosteroids, anti-inflammatory drugs, hypertension drugs, anesthetics, hypnotic sedatives, tranquilizers, antibacterial substances, antifungal substances, skin stimulants, inflammation inhibitors, anti-epileptics, analgesics, antipyretics, anesthetics, mold inhibitors, antimicrobial antibiotics, vitamins, antiviral agents, swelling improvers, diuretics, antihypertensives, coronary vasodilators, anti-tussive expectorants, slimming agents, anti-histamines, antiarrhythmic agents, cardiotonics, adrenocortical hormones, blood circulation promoters, local anesthetics, fat-splitting components, and mixtures thereof. However, it should not be construed that the invention is limited thereto. These drugs are used singly or in admixture of two or more kinds thereof as the need arises.

The content of such a functional substance is not particularly limited so far as it falls within the range where the effect of a medicine can be expected. However, from the viewpoints of adhesive strength as well as pharmacological effect and economy, the content of the functional substance is preferably from 0.01 to 25 parts by weight, and more preferably from 0.5 to 15 parts by weight based on 100 parts by weight of the adhesive.

Furthermore, a method for providing the adhesive layer is not limited so far as a thermal packaging body for joint surroundings can be fixed. The adhesive layer may be entirely provided or partially or intermittently provided. Examples of its shape include various shapes such as a network-like shape, a stripe-like shape, a dot-like shape, and strip-like shape.

The heat generating body of the invention can be used outside an inner layer of clothes, can be used inside an inner layer of clothes or can be used upon patching on the body. If desired, the heat generating body can be designed such that the fixing relation between the heat generating body and the body of a user can be used for each purpose. Furthermore, by providing irregularities in the exothermic part by the sectional exothermic parts and the sectioned part, the heat generating body of the invention is designed such that a fixed temperature is produced regardless of the surface of the heat generating body on which the installation measure is provided. The heat generating body of the invention may be worn in clothes of a user and brought into direct contact with the body of the user. The heat generating composition is designed so as to achieve oxidation at a specified rate for the purpose of producing a specified temperature. In the case of relaxing a pain while keeping the skin temperature at from 32 to 50° C., preferably from 32 to 45° C., and more preferably from 32 to 39° C. for from 30 seconds to 24 hours by using the heat generating body of the invention, a person who uses the heat generating body may make adequate selection. Examples of the use of the present heat generating body include the following 1) to 4).

1) In the case of warming the body by fixing the heat generating body to the inside of clothes and bringing it into direct contact with the body, an adhesive layer which is a fixing measure is provided on the air-permeable surface of the heat generating body to form an air-permeable adhesive layer surface; the heat generating body is fixed to the inside of clothes; and the other surface is brought into contact with the body, thereby directly warming the skin from the foregoing surface. In this way, since the heat generating body is not directly patched on the skin, problems such as coldness at the time of patching on the skin and the generation of itchiness or rash on the patch site are dissolved.

2) In the case of directly fixing the heat generating body to the skin of the body to warm the body, since the adhesiveness to the skin is good, a warming effect can be sufficiently enhanced, and the circulation becomes active due to the thermal effect, thereby absorbing an active substance such as a drug as contained in the adhesive layer, etc. in the blood flow. Thus, the heat generating body of the invention is also beneficial as medicinal goods for improving a local remedy effect or systemic remedy effect.

3) In the case of wearing the heat generating body on the outside of an undergarment, etc. to warm the body through clothes, since the clothes are mediated, a temperature stimulus against the skin becomes mild so that mild warmth-taking can be achieved while preventing a burn, etc. from occurring.

4) By providing the heat generating body with a belt or incorporating it into a belt, a hanging function is added. Thus, since the heat generating body can be fixed to curved surfaces such as knees, elbows, legs, arms, and the back or sites around the joints, it is possible to effectively warm, relax or remedy curved surfaces or sites around the joints.

In this way, when the heat generating body of the invention is patched on an affected part such that the sectional exothermic parts are parallel to a muscle or tendon of the affect part, a reverse physical tension against the tension of the muscle or tendon is continuously given, thereby relieving the tension of the muscle or tendon. Furthermore, a dislocation strain is brought between the muscles or tendons adjacent to each other, and the foregoing physical tension for the purpose of relieving the tension of the muscle or tendon is reinforced. As a result, residence of vital energy and blood is dissolved, and a symptom of menstrual pain is relaxed. In addition, a stimulus of a so-called "acupuncture point" by a pressing feeling by the rigidity of the sectional exothermic parts or the thickness of the sectional exothermic parts is also effective for relaxing the symptom of menstrual pain. Moreover, the heat generating body of the invention has follow-up properties and fitness to the body due to the flexibility of the sectioned part and is excellent in a feeling for use.

Furthermore, at least one of the packaging materials is made of a raw material having a breaking strength of 500 g/mm$^2$ or more, preferably 1,000 g/mm$^2$ or more, and more preferably 2,000 g/mm$^2$ or more at 25° C., with an absolute value of a difference between the breaking strength at 23° C. and the breaking strength at 60° C. being preferably not more than 50 g/mm$^2$, and having a breaking elongation of 30% or more at 90° C.

Furthermore, the packaging material is preferably a laminate of a non-woven fabric and a thermoplastic resin-made film-like material. Its thickness is not limited so far as the foregoing breaking elongation is secured. It is preferably 10 µm or more, more preferably from 10 to 100 µm, further preferably from 20 to 80 µm, still further preferably from 25 to 80 µm, even further preferably from 25 to 60 µm, and even still further preferably from 25 to 50 µm.

Though the fibrous material is not limited, it is preferably a woven fabric, a knitted fabric or a non-woven fabric. Examples of the non-woven fabric include a carded non-woven fabric, a spunbonded non-woven fabric, an air-laid non-woven fabric, a heat bonded non-woven fabric, a water twisted non-woven fabric, a melt swollen non-woven fabric, and/or an air-through bonded non-woven fabric. Examples of the material composition thereof include cotton, polyesters, polyethylene, polypropylene, and nylons. In particular, soft and flexible materials are preferable. Furthermore, as a material which constitutes the surface coming into contact with the skin, a material which is soft, easily warps and does not cause inflammation on the skin is preferable. The non-woven fabric on the surface which comes into contact with the skin is preferably a napped non-woven fabric.

The film-like material is a material resulting from co-extrusion molding of polyethylene, polypropylene, a nylon, a polyester, polyvinyl chloride, polyvinylidene chloride, polyurethane or polystyrene and a heat seal layer of a saponified ethylene-vinyl acetate copolymer, an ethylene-vinyl acetate copolymer, etc. Though the thickness of the film-like material is not limited, it is preferably about 80 µm, more preferably about 50 µm, further preferably about 40 µm, and still further preferably about 30 µm.

A material resulting from co-extrusion molding of a polyethylene layer and a polyethylene layer using a metallocene catalyst or a material resulting from co-extrusion molding of a polyethylene layer and an ethylene-vinyl acetate copolymer layer is preferable. In this case, the thickness of the polyethylene is preferably from 10% to 90%, and more preferably from about 40% to 60% of the whole thickness of the material.

The production process of a laminate of a fibrous material and a film-like material is not limited. Examples thereof include a method for directly laminating a fibrous material on a co-extrusion molded film and a method for laminating a fibrous material and a film-like material via a bonding layer such as an adhesive layer, a bonding agent layer, an air-permeable adhesive layer, and an organic bonding agent layer.

Incidentally, in this description, the polyethylene includes polyethylene as produced using a metallocene catalyst.

In particular, in the case of laminating a heat generating composition molded body (inclusive of a heat generating composition compressed body in the invention) on a packaging material not having an accommodating pocket by die molding, further putting a packaging material thereon and then sealing to prepare an exothermic part having sectional exothermic parts or a heat generating body, it is preferred to use a laminate of a thermoplastic resin-made fibrous material and a thermoplastic resin-made film-like material as at least one of the packaging materials.

It is preferable that the packaging material for die molding heat generating body is flexible but non-elastic at from 25 to 60° C., preferably has a breaking strength of 40 g/mm$^2$ or more, more preferably 500 g/mm$^2$ or more, and further preferably 800 g/mm$^2$ or more at 25° C. and has a breaking elongation of 20% or more at 90° C. The breaking elongation at 90° C. is preferably 30% or more, more preferably 50% or more, further preferably 100% or more, and still further preferably 150% or more. In this way, when the periphery of the heat generating composition molded body is heat sealed, the packaging material can be stretched in an amount necessary for heat sealing due to the remaining heat. Thus, the periphery of the heat generating composition molded body can be heat sealed without causing seal cut, and the shape of the heat generating body can be kept at the time of using the heat generating body.

The "film-like material" as referred to herein means a material resulting from forming the raw material as described in the foregoing substrate or covering material into a film-like shape; and examples of the fibrous material include non-woven fabrics and fabrics. The lamination method is not limited. Examples thereof include a method for using it at the time of preparing a packaging material to be used for a heat generating body such as chemical body warmers.

The air permeability is not limited so far as the heat generation can be kept. In the case of use in usual heat generation, the air permeability is usually from 50 to 10,000 g/m$^2$/24 hr, preferably from 70 to 5,000 g/m$^2$/24 hr, more preferably from 100 to 2,000 g/m$^2$/24 hr, and further preferably from 100 to 700 g/m$^2$/24 hr in terms of moisture permeability by the Lyssy method.

When this moisture permeability is less 50 g/m$^2$/24 hr, the heat value is small and a sufficient thermal effect is not obtained, and therefore, such is not preferable. On the other hand, when it exceeds 10,000 g/m$^2$/24 hr, the exothermic temperature is high so that a problem in safety may possibly be generated, and therefore, such is not preferable.

The heat generating composition is not limited so far as it is a heat generating composition which contains, as essential components, an iron powder, a carbon component, a reaction accelerator and water, does not contain a flocculent aid, a dry binding agent, a flocculant, an adhesive binder, a thickener and an excipient, contains the surplus water so as to have a water mobility value of from 0.01 to 20, has moldability due to the surplus water, with the water in the moldable heat generating composition not functioning as a barrier layer, and is capable of causing an exothermic reaction upon contact with air.

Incidentally, in the invention, what water does not function as a barrier layer and causes an exothermic reaction upon contact with air means that water in a heat generating composition does not function as a barrier layer which is an air intercepting layer and immediately after the production of a heat generating composition, comes into contact with air, thereby immediately causing an exothermic reaction.

In addition, if desired, at least one member selected from additional components consisting of a water retaining agent, a water absorptive polymer, a pH adjusting agent, a hydrogen formation inhibitor, an aggregate, a fibrous material, a functional substance, a surfactant, an organosilicon compound, a pyroelectric substance, a moisturizer, a fertilizer component, a hydrophobic polymer compound, a heat generating aid, a metal other than iron, a metal oxide other than iron oxide, an acidic substance, and a mixture thereof may be further added to the heat generating composition.

Furthermore, in the heat generating composition of the invention or the like, although there is no particular limitation for the compounding ratio thereof, it is preferred to select the compounding ratio such that the amount of the reaction accelerator is from 1.0 to 50 parts by weight, the amount of water is from 1.0 to 60 parts by weight, the amount of the carbon component is from 1.0 to 50 parts by weight, the amount of the water retaining agent is from 0.01 to 10 parts by weight, the water absorptive polymer is from 0.01 to 20 parts by weight, the amount of the pH adjusting agent is from 0.01 to 5 parts by weight, and the amount of the hydrogen formation inhibitor is from 0.01 to 12 parts by weight, respectively based on 100 parts by weight of the iron powder; and that the heat generating composition has a water mobility value of from 0.01 to 20.

In addition, the following components may be added in compounding ratios as described below to the iron powder to the heat generating composition. That is, the amount of the metal other than iron is from 1.0 to 50 parts by weight, the amount of the metal oxide other than iron oxide is from 1.0 to 50 parts by weight, the amount of the surfactant is from 0.01 to 5 parts by weight, the amount of each of the hydrophobic polymer compound, the aggregate, the fibrous material, the functional substance, the organosilicon compound and the pyroelectric substance is from 0.01 to 10 parts by weight, the amount of each of the moisturizer, the fertilizer component and the heat generating aid is from 0.01 to 10 parts by weight, and the amount of the acidic substance is from 0.01 to 1 part by weight based on 100 parts by weight of the iron powder. Incidentally, a magnetic material may further be compounded, and its compounding ratio may be properly determined depending upon the desire.

Incidentally, these compounding ratios can also be applied in a reaction mixture and a heat generating mixture. Furthermore, a water mobility value of the reaction mixture is usually less than 0.01.

As the water, one from a proper source may be employed. Its purity and kind and the like are not particularly limited.

In the case of the heat generating composition, the content of water is preferably from 1 to 70% by weight, more preferably from 1 to 60% by weight, further preferably from 7 to 60% by weight, still further preferably from 10 to 50% by weight, and even further preferably from 20 to 50% by weight of the heat generating composition.

Furthermore, in the case of the reaction mixture or heat generating mixture prior to the contact treatment with an oxidizing gas, the content of water is preferably from 0.5 to 20% by weight, more preferably from 1 to 20% by weight, further preferably from 3 to 20% by weight, and still further preferably from 4 to 15% by weight of the reaction mixture or heat generating mixture.

The carbon component is not particularly limited so far as it contains carbon as a component. Examples thereof include carbon black, graphite, active carbon, carbon nanotubes, carbon nanohorns, and flullerenes. Carbon which has become conductive by doping or the like is also employable. There are enumerated active carbons as prepared from coconut shell, wood, charcoal, coal, bone carbon, etc. and carbons as prepared from other raw materials such as animal products, natural gases, fats, oils, and resins. In particular, active carbons having an adsorption retaining ability are preferable.

Furthermore, it is not always required that the carbon component is present alone. In the case where an iron powder containing the carbon component and/or covered by the carbon component is used in the heat generating composition, it is to be noted that the heat generating composition contains the carbon component even though the carbon component is not present alone.

The reaction accelerator is not particularly limited so far as it is able to promote the reaction of the heat generating substance. Examples thereof include metal halides, nitrates, acetates, carbonates, and metal sulfates. Examples of metal halides include sodium chloride, potassium chloride, magnetic chloride, calcium chloride, ferrous chloride, ferric chloride, sodium bromide, potassium bromide, ferrous bromide, ferric bromide, sodium iodide, and potassium iodide. Examples of nitrates include sodium nitrate and potassium nitrate. Examples of acetates include sodium acetate. Examples of carbonates include ferrous carbonate. Examples of metal sulfates include potassium sulfate, sodium sulfate, and ferrous sulfate.

The water retaining agent is not limited so far as it is able to retain water. Examples thereof include porous materials derived from plants having high capillary function and hydrophilicity such as wood meal, pulp powder, active carbon, saw dust, cotton cloth having a number of cotton fluffs, short fiber of cotton, paper dust, and vegetable materials, water-containing magnesium silicate based clay minerals such as active clay and zeolite, pearlite, vermiculite, silica based porous substances, coralline stone, and volcanic ash based substances (for example, terraballoon, shirasu balloon, and taisetsu balloon). In order to increase a water retaining ability and enhance a shape holding ability of such a water retaining agent, the water retaining agent may be subjected to a processing treatment such as baking and/or pulverization.

The water absorptive polymer is not particularly limited so far as it is a resin having a crosslinking structure and having a water absorption magnification of ion-exchanged water of 3 times or more of the dead weight. Furthermore, a water absorptive polymer the surface of which is crosslinked may be employed. Conventionally known water absorptive polymers and commercial products may also be employed.

Examples of the water absorptive polymer include poly(meth)acrylic acid crosslinked materials, poly(meth)acrylic acid salt crosslinked materials, sulfonic group-containing poly(meth)acrylic ester crosslinked materials, polyoxyalkylene group-containing poly(meth)acrylic ester crosslinked materials, poly(meth)acrylamide crosslinked materials, crosslinked materials of a copolymer of a (meth)acrylic acid salt and a (meth)acrylamide, crosslinked materials of a copolymer of a hydroxyalkyl (meth)acrylate and a (meth)acrylic acid salt, polydioxolane crosslinked materials, crosslinked polyethylene oxide, crosslinked polyvinylpyrrolidone, sulfonated polystyrene crosslinked materials, crosslinked polyvinylpyridine, saponification products of a starch-poly(meth) acrylonitrile graft copolymer, starch-poly(meth)acrylic acid (salt) graft crosslinked copolymers, reaction products of polyvinyl alcohol and maleic anhydride (salt), crosslinked polyvinyl alcohol sulfonic acid salts, polyvinyl alcohol-acrylic acid graft copolymers, and polyisobutylene maleic acid (salt) crosslinked polymers. These water absorptive polymers may be used alone or in combination with two or more kinds thereof.

Of these water absorptive polymers, water absorptive polymers having biodegradation properties are not limited so far as they are a biodegradable water absorptive polymer. Examples thereof include polyethylene oxide crosslinked materials, polyvinyl alcohol crosslinked materials, carboxymethyl cellulose crosslinked materials, alginic acid crosslinked materials, starch crosslinked materials, polyamino acid crosslinked materials, and polylactic acid crosslinked materials.

The pH adjusting agent is not limited so far it is able to adjust the pH. Examples thereof include alkali metal weak acid salts and hydroxides and alkaline earth metal weak acid salts and hydroxides such as $Na_2CO_3$, $NaHCO_3$, $Na_3PO_4$, $Na_2HPO_4$, $Na_5P_3O_{10}$, NaOH, KOH, $Ca(OH)_2$, $Mg(OH)_2$, and $Ca_3(PO_4)_2$.

The hydrogen formation inhibitor is not limited so far as it is able to inhibit the formation of hydrogen. Examples thereof include one member or two or more members selected from the group consisting of sulfur compounds, oxidizing agents, alkaline substances, sulfur, antimony, selenium, phosphorus, and tellurium. Incidentally, examples of sulfur compounds include compounds with an alkali metal or an alkaline earth metal, metal sulfides such as calcium sulfide, metal sulfites such as sodium sulfite, and metal thiosulfates such as sodium thiosulfate.

Examples of the oxidizing agent include nitrates, oxides, peroxides, halogenated oxygen acid salts, permanganates, and chromates.

The aggregate is not limited so far as it is useful as a filler and/or is useful for making the heat generating composition porous. Examples thereof include fossilized coral (for example, coral fossil and weathered coral fossil), bamboo charcoal, bincho charcoal, silica-alumina powders, silica-magnesia powders, kaolin, crystalline cellulose, colloidal silica, pumice, silica gel, silica powders, mica powders, clays, talc, synthetic resin powders or pellets, foamed synthetic resins such as foamed polyesters or polyurethanes, diatomaceous earth, alumina, and cellulose powder. Incidentally, it is to be noted that kaolin and crystalline cellulose are not contained in the heat generating composition of the invention.

The fibrous material is an inorganic fibrous material and/or an organic fibrous material. Examples thereof include rock wool, glass fibers, carbon fibers, metal fibers, pulps, papers, non-woven fabrics, woven fabrics, natural fibers such as cotton and hemp, regenerated fibers such as rayon, semi-synthetic fibers such as acetates, synthetic fibers, and pulverized products thereof.

The functional substance is not limited so far as it is a substance having any function. Examples thereof include at least one member selected from minus ion emitting substances and far infrared ray radiating substances. The minus ion emitting substance is not limited so far as it emits a minus ion as a result either directly or indirectly, and examples thereof include ferroelectric substances such as tourmaline, fossilized coral, granite, and calcium strontium propionate, and ores containing a radioactive substance such as radium and radon. The far infrared ray radiating substance is not limited so far as it radiates far infrared rays. Examples thereof include ceramics, alumina, zeolite, zirconium, and silica.

The surfactant includes anionic surfactants, cationic surfactants, nonionic surfactants, and ampholytic surfactants. Especially, nonionic surfactants are preferable, and examples thereof include polyoxyethylene alkyl ethers, alkylphenol-ethylene oxide adducts, and higher alcohol phosphoric acid esters.

The organosilicon compound is not limited so far as it is a compound having at least an Si—O—R bond and/or an Si—N—R bond and/or an Si—R bond. The organosilicon compound is in the form of a monomer, a lowly condensed product, a polymer, etc. Examples thereof include organosilane compounds such as methyltriethoxysilane; and dimethylsilicone oil, polyorganosiloxane, or silicone resin compositions containing the same.

The pyroelectric substance is not limited so far as it has pyroelectricity. Examples thereof include tourmaline, hemimorphic ores, and pyroelectric ores. Tourmaline or achroite which is a kind of tourmaline is especially preferable. Examples of the tourmaline include dravite, schorl, and elbaite.

The moisturizer is not limited so far as it is able to hold moisture. Examples thereof include hyaluronic acid, collagen, glycerin, and urea.

The fertilizer component is not limited so far as it is a component containing at least one of three elements of nitrogen, phosphorus and potassium. Examples thereof include a bone powder, urea, ammonium sulfate, calcium perphosphate, potassium chloride, and calcium sulfate.

The hydrophobic polymer compound is not limited so far as it is a polymer compound having a contact angle with water of 40° or more, preferably 50° or more, and more preferably 60° or more in order to improve the draining in the composition. The shape of the hydrophobic polymer compound is not limited, and examples thereof include powdery, particulate, granular, and tablet shapes. Examples of the hydrophobic polymer compound include polyolefins such as polyethylene and polypropylene, polyesters, and polyamides.

Examples of the heat generating aid include metal powders, metal salts, and metal oxides such as Cu, Mn, $CuCl_2$, $FeCl_2$, manganese dioxide, cupric oxide, triiron tetroxide, and mixtures thereof.

As the metal oxide other than iron oxide, any material can be employed so far as it does not hinder the oxidation of iron by an oxidizing gas, and examples thereof include manganese dioxide and cupric oxide.

The acidic substance may be any of an inorganic acid, an organic acid, or an acidic salt. Examples thereof include hydrochloric acid, sulfuric acid, nitric acid, acetic acid, oxalic acid, citric acid, malic acid, maleic acid, chloroacetic acid, iron chloride, iron sulfate, iron oxalate, iron citrate, aluminum chloride, ammonium chloride, and hypochlorous acid.

As the "iron powder" as referred to herein, usual iron powders, iron alloy powders and active iron powders such as iron powders comprising particles, a surface of each of which is at least partially covered with an oxygen-containing film and iron alloy powders comprising particles, a surface of each of which is at least partially covered with an oxygen-containing film, are preferable. Incidentally, the "iron oxide film" as referred to herein is a film made of oxygen-containing iron such as iron oxide, hydroxide or oxyhydroxide. Furthermore, the "active iron powder" as referred to herein is a powder in which an iron oxide film is formed at least locally on the surface of an iron powder, from which an oxidation reaction promoting effect is obtained by a local cell as formed between an iron matrix and an iron oxide film or a pit inside and outside the iron oxide film.

The iron powder is not limited, and examples thereof include cast iron powders, atomized iron powders, electrolyzed iron powders, reduced iron powders, sponge iron powders, and iron alloy powders thereof. In addition, the iron powder may contain carbon or oxygen, and an iron powder containing 50% or more of iron and other metals may be employed. The kind of the metal which is contained as an alloy, etc. is not particularly limited so far as the iron component works as a component of the heat generating composition. Examples of such a metal include metals such as aluminum, manganese, copper, nickel, silicon, cobalt, palladium, and molybdenum, and semiconductors. The metal of the invention includes a semiconductor. Such a metal or alloy may be contained only in the surface or the interior, or may be contained in both the surface and the interior.

In the iron powder of the invention, the content of the metal other than iron is usually from 0.01 to 50% by weight, and preferably from 0.1 to 10% by weight based on the whole of the iron powder.

Examples of the iron powder having an oxygen-containing film on at least a part of the surface of the iron include:

(A) an active iron powder in which the surface of an iron component is at least partially oxidized, which is obtained by contact treating the essential components of the heat generating composition or the essential components to which acidic substances or other necessary components are added with an oxidizing gas, thereby partially oxidizing the iron component;

(B) an active iron powder in which the content of wustite is from 2 to 50% by weight in terms of an X-ray peak intensity ratio to iron;

(C) an iron powder having an iron oxide film having a thickness of 3 nm or more on the surface thereof; and (D) a mixture of an active iron powder and an iron powder other than an active iron powder.

With respect to (A), although the mechanism is not elucidated in detail, it is assumed that upon contact between the oxidizing gas and the components, not only an iron oxide film, namely, an oxygen-containing film is formed on the surface of the iron powder due to the oxidation of the components, especially the oxidation of the iron powder, but also the surface of active carbon is oxidized and/or the oxidized iron component is adhered, whereby hydrophilicity is imparted or improved, and coupling between the components or structurization takes place through the mediation of water.

That is, it is assumed that some kind of a change in the function occurs such that an iron oxide film is formed on the surface of the iron powder, the shape of the iron powder particle becomes irregular, a strain is generated due to the oxidation, or a water-containing pit is formed, whereby the iron powder is activated and exothermic rising properties are improved.

Furthermore, the case where magnetite ($Fe_3O_4$) is present in the iron oxide film is preferable because the conductivity is excellent, and the case where hematite ($Fe_2O_3$) is present in the iron oxide film is also preferable because the iron oxide film becomes porous. Moreover, it is assumed that the carbon component is oxidized on the surface thereof and becomes a carbon component which is rich in oxides on the surface thereof, whereby the hydrophilicity increases and the activity increases.

The thickness of the iron oxide film which is an oxygen-containing film covering the surface of the iron powder, as measured by the Auger electron spectroscopy, is usually 3 nm or more, preferably from 3 nm to 100 μm, more preferably from 30 nm to 100 μm, further preferably from 30 nm to 50 μm, still further preferably from 30 nm to 1 μm, even further preferably from 30 nm to 500 nm, and even still further preferably from 50 nm to 300 nm.

When the thickness of the oxygen-containing film of iron is 3 nm or more, the thickness of the oxygen-containing film of iron is able to exhibit a promoting effect of the oxidation reaction, and upon contact with an oxidizing gas such as air, is able to immediately initiate the oxidation reaction. When the thickness of the oxygen-containing film of iron is 100 μm or more, though the heat generation time may possibly be shortened, such is applicable depending upon the utility.

Furthermore, according to the active iron powder, by using a reaction mixture containing, as essential components, an iron powder, a reaction accelerator and water and having a water content of from 0.5 to 20% by weight and a water mobility value showing a surplus water content of less than 0.01, the reaction rate at the time of the contact treatment with an oxidizing gas can be raised, thereby achieving a time required for regulating a temperature rise of the reaction mixture at 1° C. or more within 10 minutes. By shortening a time required for arrival at a prescribed temperature or higher, proper activation can be achieved, and unnecessary oxidation on the iron powder can be prevented.

Furthermore, the heat generating composition prepared by adding a carbon component, etc. to a heat generating mixture as produced by contact treating the reaction mixture with an oxidizing gas or adjusting the water content so as to have a water mobility value of from 0.01 to 50 is properly tacky, has excellent moldability and is able to be applied with a molding method such as a force-through die molding method and a cast molding method, whereby heat generating bodies of various shapes can be produced. In particular, a heat generating composition having a water mobility value of from 0.01 to 20 is excellent because it initiates an exothermic reaction immediately after contacting with air, has excellent exothermic rising properties and has excellent moldability.

The contact treatment method of the reaction mixture with an oxidizing gas is not particularly limited so far as it is able to contact treat a reaction mixture containing, as essential components, an iron powder, a reaction accelerator and water and having a water content of from 0.5 to 20% by weight and a water mobility value of less than 0.01 with an oxidizing gas and regulate a temperature rise of the reaction mixture at 1° C. or more.

Specific Examples Thereof Include:

(1) a process for producing a heat generating mixture containing an iron powder having an iron oxide film on the surface thereof by subjecting a reaction mixture of an iron powder, a reaction accelerator and water in an oxidizing gas atmosphere to a self-exothermic reaction, thereby partially oxidizing the iron powder;

(2) a process for producing a heat generating mixture by subjecting a reaction mixture of an iron powder, a reaction accelerator, an acidic substance and water in an oxidizing gas atmosphere to a self-exothermic reaction;

(3) a process for producing a heat generating mixture by subjecting a reaction mixture of an iron powder, a reaction accelerator, a carbon component and water in an oxidizing gas atmosphere to a self-exothermic reaction;

(4) a process for producing a heat generating mixture by subjecting a reaction mixture of an iron powder, a reaction accelerator, an acidic substance, a carbon component and water in an oxidizing gas atmosphere to a self-exothermic reaction;

(5) a process for producing a heat generating mixture containing a partially oxidized iron powder by carrying out the method as set forth above in any one of (1) to (4), wherein the reaction mixture or heat generating mixture as set forth above in any one of (1) to (4) contains a component other than the foregoing components;

(6) a process for producing a heat generating mixture by carrying out the method as set forth above in any one of (1) to (5) under circumstances heated so as to have temperature of at least 10° C. higher than the circumferential temperature;

(7) a process for producing a heat generating mixture by carrying out the method as set forth above in any one of (1) to (6) by blowing an oxidizing gas;

(8) a process for producing a heat generating mixture by carrying out the method as set forth above in (7) by blowing the oxidizing gas heated so as to have a temperature of at least 10° C. higher than the circumferential temperature;

(9) a process for producing a heat generating composition by carrying out the method as set forth above in any one of (1) to (8) by contact treating with an oxidizing gas until the temperature exceeds a maximum temperature which is a maximum point of temperature rise by the exothermic reaction;

(10) a process for producing a heat generating mixture by carrying out the method as set forth above in any one of (1) to (8) by contact treating with an oxidizing gas until the temperature exceeds a maximum temperature by the exothermic reaction and drops by at least 10 to 20° C. from the maximum temperature;

(11) a process for producing a heat generating composition by carrying out the method as set forth above in any one of (1) to (8) by contact treating with an oxidizing gas until the temperature exceeds a maximum temperature which is a maximum point of temperature rise by the exothermic reaction and after intercepting the oxidizing gas, holding it until the temperature of at least the reaction mixture drops by at least 10 to 20° C. from the maximum temperature; and

(12) a process for producing a heat generating mixture by heating the reaction mixture or heat generating mixture as set forth above in any one of (1) to (5) under oxidizing gas circumstances while regulating a temperature rise at 1° C. or more.

In addition, a heat generating mixture as prepared by adding other components to the heat generating mixture and further treating with an oxidizing gas may be employed.

Incidentally, the circumstances of the reaction mixture at the time of contact treatment with an oxidizing gas are not limited so far as the reaction mixture is brought into contact with an oxidizing gas under circumstances of 0° C. or higher and a temperature rise of the reaction mixture is regulated at 1° C. or more within 10 minutes. In the case where the contact treatment is carried out in an open system, the circumstances may be either the state that the reaction mixture is present in a lid-free vessel or the state that an oxidizing gas such as air comes into a vessel through an air-permeable sheet-like material such as non-woven fabrics.

Furthermore, the contact treatment with an oxidizing gas may be carried out with or without stirring in a fluidized or non-fluidized state and may be carried out in a batch or continuous system.

Examples of the Final Heat Generating Composition Include:

1) a heat generating composition containing, as a heat generating composition raw material, a heat generating mixture produced in the process as set forth above in any one of (1) to (12);

2) a heat generating composition obtained by adding other components to the heat generating composition as set forth above in 1); and 3) a heat generating composition obtained by adjusting the water content of the heat generating composition as set forth above in 1) or 2).

The order of the timing of adding other components than the essential components and the timing of adjusting the water content is not limited.

Here, the water content in the reaction mixture and also the heat generating mixture prior to the treatment with an oxidizing gas is usually from 0.5 to 20% by weight, preferably from 1 to 15% by weight, more preferably from 2 to 10% by weight, further preferably from 3 to 10% by weight, and still further preferably from 6 to 10% by weight.

The temperature of the reaction mixture after the contact with an oxidizing gas is not limited so far as the temperature rise is regulated at 1° C. or more. The temperature of the reaction mixture after the contact with an oxidizing gas is preferably from 1 to 80° C., more preferably from 1 to 70° C., further preferably from 1 to 60° C., and still further preferably from 1 to 40° C.

The circumferential temperature at the time of contact between the reaction mixture and the oxidizing gas is not limited so far as the temperature of the reaction mixture is raised to a prescribed temperature or higher. The circumferential temperature at the time of contact between the reaction mixture and the oxidizing gas is preferably 0° C. or higher, more preferably from 0 to 250° C., further preferably from 10 to 200° C., still further preferably from 20 to 150° C., even further preferably from 25 to 100° C., and even still further preferably from 25 to 50° C.

The time of contact between the reaction mixture and the oxidizing gas is not limited so far as the time required for regulating a temperature rise at 1° C. or more is within 10 minutes. The time of contact between the reaction mixture and the oxidizing gas is preferably from one second to 10 minutes, more preferably from one second to 7 minutes, further preferably from one second to 5 minutes, still further preferably from 2 seconds to 5 minutes, even further preferably from 2 seconds to 3 minutes, and even still further preferably from 2 seconds to one minute.

The temperature of the oxidizing gas is not limited so far as the foregoing circumferential temperature is kept.

As the "oxidizing gas" as referred to herein, any gas can be used as the oxidizing gas so far as it is oxidizing. Examples thereof include an oxygen gas, air, and mixed gases of an inert gas (for example, a nitrogen gas, an argon gas, and a helium gas) and an oxygen gas. Although the mixed gas is not limited so far as it contains oxygen, mixed gases containing 10% or more of an oxygen gas are preferable, and of these, air is especially preferable. If desired, a catalyst such as platinum, palladium, iridium, and compounds thereof can also be used.

The oxidation reaction can be carried out under stirring in an oxidizing gas atmosphere optionally under a pressure and/or upon irradiation of ultrasonic waves.

The optimal condition of the oxidation reaction may be properly experimentally determined.

An amount of the oxidizing gas to be used is not limited but may be adjusted depending upon the kind of the oxidizing gas, the kind and particle size of the iron powder, the water content, the treatment temperature, the treatment method, and the like.

In the case of an open system, there is no limitation so far as a necessary amount of oxygen can be taken in. In order to prevent fly of the reaction mixture or contamination of dusts, etc., the system may be surrounded by an air-permeable raw material such as non-woven fabrics and woven fabrics. So far as the system is in an air-permeable state, it is to be noted that the system is an open system.

In the case where air is used in the system of blowing an oxidizing gas, for example, the amount of air is preferably from 0.01 to 1,000 L/min, more preferably from 0.01 to 100 L/min, and further preferably from 0.1 to 50 L/min per 200 g of the iron powder under one atmosphere. In the case of other oxidizing gas, the amount of the oxidizing gas may be converted on the basis of the case of air.

If desired, a peroxide may be added. Examples of the peroxide include hydrogen peroxide and ozone.

Here, so far as the iron powder is partially oxidized, the state of the reaction mixture or heat generating mixture at the time of the contact treatment with an oxidizing gas may be any of a standing state, a transfer state, or a fluidizing state by stirring, etc. and may be properly selected. Furthermore, the circumstances at the time of mixing the respective components of the reaction mixture, the heat generating mixture or the heat generating composition and at the time of the contact treatment with a mixed oxidizing gas at the time of adjusting the water content are not limited, and examples thereof include those in an oxidizing gas atmosphere and those in blowing of an oxidizing gas.

A method for measuring a temperature rise of the heat generating composition is as follows.

1) A heat generating composition is allowed to stand in a state that it is sealed in an air-impermeable outer bag for one hour under a condition that the circumferential temperature is $20 \pm 1°$ C.

2) A magnet is provided in the vicinity of a central part of the back side of a polyvinyl chloride-made supporting plate (3 mm in thickness×600 mm in length×600 mm in width) of a footed supporting table so as to cover a cavity shape of a molding die.

3) A temperature sensor is placed on the central part of the supporting plate.

4) A polyethylene film (25 μm in thickness×250 mm in length×200 mm in width) as provided with an adhesive layer having a thickness of about 80 μm is stuck onto the supporting plate via a sticky layer such that the center of the polyethylene film is positioned at the sensor.

5) The heat generating composition is taken out from the outer bag.

6) A template (250 mm in length×200 mm in width) having a cavity (80 mm in length×50 mm in width×3 mm in height) is placed above the central part of the polyethylene film; a sample is placed in the vicinity of the cavity; a force-in die plate is moved along the template; the sample is charged into the cavity while stuffing; and the sample is leveled while stuffing along the template plane (force-in die molding), thereby filling the sample in the die. Next, the magnet beneath the supporting plate is removed, and the temperature measurement is started.

With respect to the measurement of the exothermic temperature, the temperature is measured for 10 minutes at a measurement timing of 2 seconds using a data collector, and exothermic rising properties are judged in terms of the temperature after elapsing 3 minutes.

The heat generation test of the heat generating body follows the JIS temperature characteristic test.

In the iron powder or active iron powder in the oxidizing gas-treated heat generating composition, at least a part of the surface thereof is covered by an oxygen-containing film of iron. The degree of covering on the surface of the oxygen-containing film of iron is not limited so far as at least a part of the surface thereof is covered, and the surface may be entirely covered. In the case of the heat generating composition of the invention, since an ion of the reaction accelerator such as a chlorine ion is contained in the heat generating composition, there is no corrosion effect of the oxide film due to anti-corrosion effect by the ion of the reaction accelerator such as a chlorine ion. Thus, the oxidation reaction which is a sort of corrosion is not hindered. In particular, in the case where an oxygen-containing film of iron is prepared while the ion of the reaction accelerator such as a chlorine ion exists together, the subject effect is large. In the case where a metal other than iron is present on the surface, it is only required that at least other part of the metal portion other than iron is covered by the oxygen-containing film of iron.

In the iron powder of the invention, not only a region where (1) entire (uniform) corrosion, (2) pitting or crevice corrosion, (3) stress corrosion cracking, or the like is generated, but also irregularities or crevices are formed. For that reason, it is assumed that the iron powder of the invention has hydrophilicity and oxidation catalytic properties (FeO, etc.) in its own portion. In producing the heat generating composition, it is important that the iron powder has an oxygen-containing film in its own portion without relying upon mixing. In particular, in the iron component as prepared by contact treating the iron component and the reaction accelerator and water as essential components with an oxidizing gas, it is thought that a reaction active part composed mainly of an oxide, a hydroxide, a chlorine ion, a hydrogen ion, etc. is formed, whereby exothermic reactivity and hydrophilicity are improved and exothermic rising properties and moldability are remarkably improved.

With respect to (B), the amount of FeO (wustite) which is contained in the iron component containing a prescribed amount of wustite is usually from 2 to 50% by weight, preferably from 2 to 40% by weight, more preferably from 2 to 30% by weight, further preferably from 5 to 30% by weight, and still further preferably from 6 to 30% by weight in terms of an X-ray peak intensity ratio of iron. When the amount of FeO (wustite) exceeds 50% by weight, though the exothermic rising properties are good, the duration of heat generation becomes short. On the other hand, when it is less than 2% by weight, the exothermic rising properties become dull.

The thickness of the oxygen-containing film of a prescribed amount or the oxygen-containing film of iron powder containing wustite and the amount of wustite are applied to the heat generating composition or the heat generating composition molded body at the time of lamination.

An iron powder containing a carbon component and/or covered by a carbon component is also preferable. Although a proportion of the carbon component is not limited so far as a ratio of the iron component to the carbon component is 50% by weight or more, an iron powder in which the surface thereof is partially covered by from 0.3 to 3.0% by weight of a conductive carbonaceous substance is useful. Examples of the conductive carbonaceous substance include carbon black, active carbon, carbon nanotubes, carbon nanohorns, and flullerenes. Ones which have become conductive by doping are also employable. Examples of the iron powder include reduced iron powders, atomized iron powders, and sponge iron powders. In particular, the case where the conductive carbonaceous substance is active carbon and the iron powder is a reduced iron powder is useful as a heat generating body.

Furthermore, in order to efficiently carry out covering by a conductive carbonaceous substance, an oil such as a spindle oil may be added in an amount of from 0.01 to 0.05% by weight to such an extent that the fluidity of the iron powder is not hindered.

In the case of measuring the water mobility value of the heat generating composition in the heat generating body and the thickness and amount of wustite of the iron oxide film of iron powder in the mixture or the heat generating composition in the heat generating body, the heat generating composition or mixture may be measured according to the following items.

1) Water Mobility Value:

The heat generating composition is taken out from the heat generating body and measured according to the foregoing method of measuring a water mobility value.

2) Thickness and Amount of Wustite of Iron Oxide Film of Iron Powder:

A measuring sample as prepared by dispersing the heat generating composition, the heat generating composition molded body, the heat generating composition compression molded body or the mixture in nitrogen-purged ion-exchanged water in a nitrogen atmosphere, separating the iron powder using a magnet and drying the iron powder in a nitrogen atmosphere is used.

The heat generating composition of the invention contains, as essential components, an iron powder, a carbon component, a reaction accelerator and water, and its production process is one which can be put into practical use on an industrial scale. A reaction mixture containing, as essential components, an iron powder, a reaction accelerator and water and having a water content of from 1 to 20% by weight and a water mobility value showing a surplus water content of less than 0.01 is brought into contact with an oxidizing gas under circumstances at 0° C. or higher, a temperature rise of the reaction mixture is regulated at 1° C. or more within 10 minutes to produce a heat generating mixture, and the subject heat generating mixture is used as a raw material to form a heat generating composition. Alternatively, a heat generating composition may be formed by subsequently further adjusting the water content, or by further adding a carbon component, etc. and adjusting the water content.

In the invention, it has become possible to realize the contact treatment with an oxidizing gas within a short period of time by regulating the water content of the reaction mixture at a fixed amount or less, especially regulating the surplus water content of the reaction mixture at a fixed amount or less and carrying out an oxidizing contact treatment. By specifying the surplus water content and performing the treatment within a short period of time, adverse influences such as poor initial exothermic rising of the heat generating composition and shortening of the heat generation-retaining time can be avoided. Thus, it has become possible to establish an industrial mass-production process. Furthermore, although stirring or the like may not be achieved during the contact treatment with an oxidizing gas, when stirring or the like is achieved, the contact treatment with an oxidizing gas can be surely carried out.

Here, so far as the iron powder is partially oxidized, the state of the reaction mixture or heat generating mixture at the time of the contact treatment with an oxidizing gas may be any of a standing state, a transfer state, or a fluidizing state by stirring, etc. and may be properly selected. Furthermore, the circumstances at the time of mixing the respective components of the reaction mixture, the heat generating mixture or the heat generating composition and at the time of mixing at the time of adjusting the water content are not limited, and examples thereof include those in an oxidizing gas atmosphere and those in blowing of an oxidizing gas.

The "adjustment of the water content" as referred to herein means that after contact treating the heat generating mixture with an oxidizing gas, water or an aqueous solution of a reaction accelerator is added. Although the amount of addition of water or an aqueous solution of a reaction accelerator is not limited, examples thereof include the addition of a weight corresponding to a reduced weight by the contact treatment and the addition of a weight such that a desired water mobility value is obtained.

Whether or not the adjustment of the water content is introduced may be properly determined depending upon the utility.

The heat generating composition of the invention contains, as essential components, an iron powder, a carbon component, a reaction accelerator and water and is started from a mixture obtained by contact treating a reaction mixture containing, as essential components, an iron powder, a reaction accelerator and water with an oxidizing gas. The heat generating composition of the invention is usually one obtained by adjusting the water content of a heat generating mixture and is a heat generating composition which is satisfactory in the exothermic rising, has a suitable amount of surplus water and has excellent moldability. Furthermore, it is possible to produce a heat generating body which can become promptly warm at the time of use.

Accordingly, at least the iron powder further including the carbon component has a history of oxidation by the contact treatment with an oxidizing gas, and it is thought that this is deeply related to excellent exothermic rising properties, exothermic endurance and excellent moldability.

When the iron powder which is contact treated with an oxidizing gas according to the invention is used, the amount of addition of the carbon component (for example, active carbon) in the heat generating composition can be reduced by, for example, 20% or more. By reducing the amount of addition of the carbon component, the costs are lowered.

According to the production process of the heat generating mixture of the invention, it is possible to obtain a heat generating composition having excellent exothermic rising properties, excellent hydrophilicity, and excellent moldability. In particular, a heat generating composition having remarkably excellent moldability and exothermic characteristics together can be obtained while specifying the water availability value at from 0.01 to 50, in particular 0.01 to 20.

The heat generating composition as produced by the production process of the invention is remarkably improved with respect to exothermic rising properties. Thus, the amount of addition of the carbon component (such as active carbon) in the heat generating composition can be reduced by, for example, 20% or more so that it can contribute to a reduction in costs.

Furthermore, since the hydrophilicity is remarkably improved, the moldability with a mold is remarkably improved. Thus, since after molding, collapsed pieces of the heat generating composition are not scattered on the surroundings of the heat generating composition molded body, sealing can be appropriately achieved so that a heat generating body free from sealing cut can be produced. In this way, heat generating composition molded bodies of various shapes can be produced, and heat generating bodies of various shapes are formed.

Furthermore, in view of improving the exothermic rising properties of the heat generating composition, the following are preferable.

1) A heat generating composition obtained by a contact treatment (self heat generation) of a mixture of the essential components of the heat generating composition, or a mixture of the foregoing mixture and an acidic substance or other necessary components with an oxidizing gas, a heat generating composition obtained by additionally adjusting the water content of the foregoing heat generating composition, or a heat generating composition obtained by adding and mixing other components in the foregoing heat generating composition.

2) Any one of the following active iron powders having an oxygen-containing film (for example, oxides) on at least a part of the surface thereof is used as the iron powder: (a) an iron powder having an oxygen-containing film of iron having a thickness, as measured by the Auger electron spectroscopy, of 3 nm or more on the surface thereof and (b) an iron powder having a content of wustite of from 2 to 50% by weight in terms of an X-ray peak intensity ratio to iron.

3) A mixture of an active iron powder having an oxygen-containing film (for example, oxides) on at least a part of the surface thereof and an iron powder not having an oxygen-containing film is used as the iron powder. In this case, a mixture containing 60% by weight or more of an active iron powder and less than 40% by weight of an iron powder other than the active iron is preferable.

In the case of storing the heat generating composition which is treated with an oxidizing gas or the heat generating composition containing an active iron powder, or a material utilizing the same over a long period of time, it is preferred to combine a hydrogen formation inhibitor therewith. This is because in this way, a heat generating body having excellent exothermic characteristics, which is inhibited in the formation of hydrogen, is free from swelling of the outer bag at the time of storage, etc. and has satisfactory exothermic rising properties, is obtained.

Furthermore, so far as the rising characteristics are not affected, the heat generating composition having a water mobility value falling outside the range of from 0.01 to 20 can contain a water-soluble polymer, a flocculant aid, a flocculant, an agglomeration aid, a dry binding material, a dry binding agent, a dry binder, an adhesive raw material, a tackifier, an excipient, a flocculating agent, or a soluble sticky raw material.

Furthermore, since a marketed heat generating body in which a heat generating composition is accommodated in an accommodating bag is provided on the assumption that it is accommodated in an outer bag which is an air-impermeable accommodating bag and is storable over a long period of time, it is preferred to use a heat generating composition containing a hydrogen formation inhibitor. Since the heat generating composition which has passed through the contact treatment with an oxidizing gas is an active composition, it is important that the heat generating composition contains a hydrogen formation inhibitor. Also, this efficacy is further strengthened by using a pH adjusting agent together.

Furthermore, so far as the reaction characteristics and exothermic characteristics are not affected, the heat generating composition having a water mobility value of less than 0.01 may contain a flocculant aid, a flocculant, an agglomeration aid, a dry binder, a dry binding agent, a dry binding material, a sticky raw material, a thickener, an excipient, or a water-soluble polymer in an amount ranging from 0.01 to 3 parts by weight respectively.

The "flocculant aid" as referred to herein is a flocculant aid as described in Japanese Patent No. 3,161,605 (JP-T-11-508314) such as gelatin, natural gum, and corn syrup.

The "flocculant" as referred to herein is a flocculent as described in JP-T-2002-514104 such as corn syrup and maltitol syrup.

The "agglomeration aid" as referred to herein is an agglomeration aid as described in JP-T-2001-507593 such as corn syrup.

The "dry binder" as referred to herein is a dry binder as described in JP-T-2002-514104 such as microcrystalline cellulose, maltodextrin, and mixtures thereof.

The "dry binding agent" as referred to herein is a dry binding agent as described in JP-T-2001-507593 such as maltodextrin and sprayed lactose.

The "dry binding material" as referred to herein is a dry binding material as described in JP-T-11-508314 such as microcrystalline cellulose, maltodextrin, and mixtures thereof.

The "sticky raw material" or the "binder" as referred to herein is a sticky raw material or binder as described in JP-A-4-293989 such as water glass, polyvinyl alcohol (PVA), and carboxymethyl cellulose (CMC).

The "thickener" as referred to herein is a thickener as described in JP-A-6-343658 such as corn starch and potato starch.

The "excipient" as referred to herein is an excipient as described in JP-A-7-194641 such as α-starch and sodium alginate.

As the "water-soluble polymer" as referred to herein, the water-soluble polymer in the adhesive layer can be used.

The particle size of the water-insoluble solid component constituting the moldable heat generating composition of the invention is not limited so far as the heat generating composition has moldability. In the case where any one of length, width and height as the size of the heat generating composition molded body as molded from the heat generating composition is small, the moldability is improved by making the particle size small.

In addition, it is preferable in view of molding that the particle size of the solid component constituting the moldable heat generating composition is small. A maximum particle size of the water-insoluble solid component exclusive of the reaction accelerator and water in the components constituting the moldable heat generating composition is preferably not more than 2.5 mm, more preferably not more than 930 μm, further preferably not more than 500 μm, still further preferably not more than 300 μm, even further preferably not more than 250 μm, and even still further preferably not more than 200 μm. Moreover, 80% or more of the particle size of the solid component is usually not more than 500 μm, preferably not more than 300 μm, more preferably not more than 250 μm, further preferably not more than 200 μm, still further preferably not more than 150 μm, and even further preferably not more than 100 μm.

Incidentally, with respect to the particle size of the water-insoluble solid component, separation is conducted using a sieve, and the particle size of the component which has passed through the sieve is calculated from an opening of the sieve. That is, sieves of 8, 12, 20, 32, 42, 60, 80, 100, 115, 150, 200, 250 and 280 meshes and a receiving dish are combined in this order from up to down. About 50 g of water-insoluble solid component particles are placed on the uppermost 8-mesh sieve and shaken for one minute using an automatic shaker. Weights of the water-insoluble solid component particles on each of the sieves and the receiving dish are weighed. The total amount thereof is defined as 100%, and the particle size distribution is determined from weight fractions. When the sum of all receiving dishes under the sieve of a specific mesh size becomes 100% which is the total sum of the particle size distribution, the size (μm) calculated from the opening of the specific mesh is defined as the particle size of the water-insoluble solid component. Incidentally, each of the mesh sieves may be combined with other mesh sieves. Here, the particles which have passed through a 16-mesh sieve are defined to have a particle size of not more than 1 mm; the particles which have passed through a 20-mesh sieve are defined to have a particle size of not more than 850 μm; the particles which have passed through a 48-mesh sieve are defined to have a particle size of not more than 300 μm; the particles which have passed through a 60-mesh sieve are defined to have a particle size of not more than 250 μm; the particles which have passed through a 65-mesh sieve are defined to have a particle size of not more than 200 μm; the particles which have passed through an 80-mesh sieve are defined to have a particle size of not more than 180 μm; the particles which have passed through a 100-mesh sieve are defined to have a particle size of not more than 150 μm; the particles which have passed through a 115-mesh sieve are defined to have a particle size of not more than 120 μm; the particles which have passed through a 150-mesh sieve are defined to have a particle size of not more than 100 μm; and the particles which have passed through a 250-mesh sieve are defined to have a particle size of not more 63 μm, respectively. The same is applicable to mesh sizes of less than these mesh sizes.

Furthermore, the heat generating composition can be classified into a powder, a granulate heat generating composition (having a water mobility value of less than 0.01), a moldable heat generating composition (having a water mobility value of from 0.01 to 20), and a sherbet-like heat generating composition (having a water mobility value exceeding 20 but not more than 50) depending upon the state of adjustment of the water content or surplus water. The heat generating composition as classified depending upon the water mobility value is as described previously.

The "moldability" as referred to in the invention exhibits that a laminate of the heat generating composition having a cavity or concave die shape can be formed by force-through molding using a trimming die having a cavity or cast molding using a concave die and after molding including mold release, the molding shape of the heat generating composition molded body is held. When the moldability is revealed, since the shape is held until the heat generating composition molded article is at least covered by a covering material and a seal part is formed between the substrate and the covering material, sealing can be achieved in the periphery of the shape with a desired shape. Also, since so-called "spots" which are a collapsed piece of the heat generating composition are not scattered in the seal part, sealing can be achieved without causing cutting in seal. The presence of the spots causes insufficient sealing.

Next, with respect to the moldability, a measurement device, a measurement method and a judgment method will be described below.

1) Measurement Device:

With respect to the measurement device, a stainless steel-made molding die (a plate having a size of 2 mm in thickness×200 mm in length×200 mm in width and having a cavity as treated by R5 in four corners of 60 mm in length×40 mm in width in a central part thereof) and a fixable leveling plate are disposed above a travelable endless belt, and magnets (two magnets having a size of 12.5 mm in thickness×24 mm in length×24 mm in width are disposed in parallel) are disposed under the endless belt. The magnets should cover a region of the leveling plate and the vicinity thereof and a region larger than a region covered by a cut side (40 mm) vertical to the advancing direction of the cavity of the molding die.

2) Measurement Method:

With respect to the measurement method, a stainless steel plate having a size of 1 mm in thickness×200 mm in length×200 mm in width is placed on the endless belt of the measurement device, a polyethylene film having a size of 70 μm in thickness×200 mm in length×200 mm in width is placed thereon, and a stainless steel-made molding die is further placed thereon. Thereafter, a leveling plate is fixed in a position of the cavity of the molding die of 50 mm far from the end portion in the advancing direction of the endless belt, 50 g of a heat generating composition is then placed in the vicinity of the leveling plate between the leveling plate and the cavity, and the heat generating composition is filled in the cavity of the molding die while leveling it by moving the endless belt at 1.8 m/min.

After the molding die has completely passed through the leveling plate, the traveling of the endless belt is stopped. Next, the molding die is removed, and a heat generating composition molded body as laminated on the polyethylene film is observed.

3) Judgment Method:

With respect to the judgment method, in the surroundings of the heat generating composition molded body, in the case where any collapsed piece of the heat generating composition molded body exceeding a maximum length of 800 μm is not present and the number of collapsed pieces of the heat generating composition molded body having a maximum length of from 300 to 800 μm is not more than 5, it is to be noted that the heat generating composition has moldability. The moldability is an essential property for a heat generating composition to be used in the molding system. If the heat generating composition does not have moldability, it is impossible to produce a heat generating body by the molding system.

The heat generating composition of the invention has resistance to compression. The "resistance to compression" as referred to herein means that a heat generating composition compressed body obtained by compressing a heat generating composition molded body as accommodated in a molding die within the die to such an extent that the thickness is 70% of the die thickness holds 80% or more of exothermic rising properties of the exothermic rising properties of the heat generating composition molded body before compression (a difference in temperature between one minute and 3 minutes after starting a heat generation test of the heat generating composition).

Here, the measurement method of exothermic rinsing properties for the resistance to compression will be described below.

1. Heat Generating Composition Molded Body:

1) A magnet is provided in the vicinity of a central part of the back side of a polyvinyl chloride-made supporting plate (3 mm in thickness×600 mm in length×600 mm in width) of a footed supporting table so as to cover a cavity shape of a molding die.

2) A temperature sensor is placed on the central part the surface of the supporting plate.

3) A polyethylene film (25 μm in thickness×250 mm in length×200 mm in width) as provided with an adhesive layer having a thickness of about 80 μm is stuck onto the supporting plate via a sticky layer such that the center of the polyethylene film is positioned at the sensor.

4) On an underlay plate (280 mm in length×150 mm in width×50 μm to 2 mm in thickness), a polyethylene film (230 mm in length×155 mm in width×25 μm to 100 μm in thickness) is placed such that one end of the polyethylene film is projected by about 20 mm outside the underlay plate and that one end thereof in the length direction is substantially coincident with one end of the underlay plate.

5) A template (230 mm in length×120 mm in width×3 mm in thickness) having a cavity (80 mm in length×50 mm in width×3 mm in height) is placed on the polyethylen film placed on the underlay plate; a template is placed on the polyethylene film such that one end thereof in the length direction is fitted to one end where the underlay plate and the polyethylene film are coincident with each other and that in the width direction, one end part of the width of the template is placed at a position of the central part by about 20 mm far from an opposing end to the side where the polyethylene film is projected outward from the underlay plate. Next, the resulting assembly is placed on the supporting plate together with the underlay plate.

6) A sample is placed in the vicinity of the cavity; a force-in die plate is moved along the molding die; the sample is charged into the cavity while stuffing; and the sample is leveled while stuffing along the template plane (force-in die molding), thereby filling the sample in the die.

7) Next, the magnet beneath the supporting plate is removed; the end portion of the projected polyethylene film is pressed; the underlay plate is removed; and the temperature measurement is started.

2. Heat Generating Composition Compressed Body:

1) to 6) are the same as in the case of the heat generating composition molded body.

8) A die having a convex having a thickness of 0.9 mm which can substantially tightly come into the cavity in relation of the cavity with an unevenness is fitted to the cavity and compressed by a roll press or plate press to prepare a heat generating composition compressed body having a thickness of 2.1 mm (compressed to 70% of the die thickness) within the die.

9) The resulting assembly is placed on the supporting plate together with the underlay plate; the magnet beneath the supporting plate is removed; the end portion of the projected polyethylene film is pressed; the underlay plate is removed; and the temperature measurement is started.

With respect to the measurement of the exothermic temperature, the temperature is measured for 5 minutes at a measurement timing of 2 seconds using a data collector, and resistance to compression is judged in terms of a difference in temperature between after elapsing one minute and after elapsing 3 minutes.

The thickness after compression is preferably from 50 to 99.5%, more preferably from 60 to 99.5%, and further preferably from 60 to 95% of the die thickness.

Incidentally, in the invention, it is to be noted that the heat generating composition molded body includes a heat generating composition compressed body.

In the sectional exothermic part or the heat generating composition molded body of the invention, its maximum width is usually from 0.5 to 60 mm, preferably from 0.5 to 50 mm, more preferably from 1 to 50 mm, further preferably from 3 to 50 mm, still further preferably 3 to 30 mm, even further preferably from 5 to 20 mm, even still further preferably from 5 to 15 mm, and most preferably from 5 to 10 mm. Furthermore, its maximum height is usually from 0.1 to 30 mm, preferably from 0.1 to 10 mm, more preferably from 0.3 to 10 mm, further preferably from 1 to 10 mm, and still further preferably from 2 to 10 mm. Moreover, its longest length is usually from 5 to 300 mm, preferably from 5 to 200 mm, more preferably from 5 to 100 mm, further preferably from 20 to 150 mm, and still further preferably from 30 to 100 mm.

A capacity of the sectional exothermic part or a volume of the heat generating composition molded body is usually from 0.015 to 500 $cm^3$, preferably from 0.04 to 30 $cm^3$, more preferably from 0.1 to 30 $cm^3$, further preferably from 1 to 30 $cm^3$, and still further preferably from 3 to 20 $cm^3$.

In the sectional exothermic part, when the sectional exothermic part which is an accommodating region of the heat generating composition is filled with the heat generating composition molded body, a volume ratio of the volume of the heat generating composition molded body which is an occupying region of the heat generating composition molded body to the capacity of the sectional exothermic part which is an accommodating region of the heat generating composition is usually from 0.6 to 1, preferably from 0.7 to 1, more preferably from 0.8 to 1, and further preferably from 0.9 to 1.0.

Furthermore, a width of the sectioned part which is a space between the sectional exothermic parts is not limited so far as sectioning can be achieved. It is usually from 0.1 to 50 mm, preferably from 0.3 to 50 mm, more preferably from 0.3 to 50 mm, further preferably from 0.3 to 40 mm, still further preferably from 0.5 to 30 mm, even further preferably from 1.0 to 20 mm, and even still further preferably from 3 to 10 mm.

Incidentally, the heat generating composition molded body or the sectional exothermic part may have any shape. The shape may be a planar shape, and examples thereof include a circular shape, an elliptical shape, a polygonal shape, a star shape, and a flower shape. Also, the shape may be a three-dimensional shape, and examples thereof include a polygonal pyramidal shape, a conical shape, a frustum shape, a spherical shape, a parallelepiped shape, a cylindrical shape, a semi-pillar shape, a semicylindroid shape, a semicylidrical shape, a pillar shape, and a cylindroid shape. Furthermore, in these shapes, the corner may be rounded, thereby processing the corner in a curvilinear or curved state, or the central part may be provided with a concave.

Furthermore, the "volume of the heat generating composition molded body of the invention" as referred to herein means a volume of the heat generating composition molded body or compressed heat generating composition molded body.

Furthermore, the "capacity of the sectional exothermic part" as referred to herein means an internal capacity of the sectional exothermic part having a heat generating composition molded body accommodated therein.

Furthermore, a heat seal part may be provided by laminating the heat generating composition molded body on a substrate, temporarily adhering a covering material to at least a part of the substrate and/or the heat generating composition molded body via an air-permeably sticky layer to provide a temporary adhering part, and heat sealing the periphery of the heat generating composition molded body. By using the foregoing non-elastic packaging material and heat sealing after the temporary adhesion, heat sealing can be surely carried out without generating wrinkles and causing seal cut. In this way, it is also possible to realize high-speed heat sealing. Furthermore, as the sticky layer, all of one which is permeable to air and one which is impermeable to air can be used. In the case where a sticky layer is provided in at least a part of the heat generating composition molded body, the sticky layer is preferably an air-permeable sticky layer. Examples of the shape include a dotted form, a cobweb form, a netlike form, and a belt-like form.

In addition, a heat generating body having a heat seal part in a narrow width may be produced by providing the temporary adhering part in a wider width than the heat seal part; performing heat sealing in a narrow width to provide a narrow heat seal part; and then pressurizing, squeezing or pressing the exothermic part by using a rod, a plate, a roll, a balloon, etc., thereby deadhering a non-heat sealed temporary adhering part and moving a part of the heat generating composition molded body into the non-heat sealed temporary adhering part.

In the invention, as a heat seal material constituting a heat seal layer, a single raw material may be used, or a composite raw material having a heat seal layer may be used. The heat seal material is not limited so far as at least a part thereof can be welded upon heating. Examples thereof include hot melt based resins such as polyolefins (for example, polyethylene and polypropylene) or olefin copolymer resins, ethylene based hot melt resins (for example, ethylene-vinyl acetate copolymer resins and ethylene-acrylic acid ester copolymer resins (for example, ethylene-isobutyl acrylate copolymer resins)), polyamide based hot melt resins, butyral based hot melt resins, polyester based hot melt resins, polyamide based hot melt resins, polyester based hot melt resins, polymethyl methacrylate based hot melt resins, polyvinyl ether based hot melt resins, polyurethane based hot melt resins, polycarbonate based hot melt resins, such as polyvinyl acetate, and vinyl chloride-vinyl acetate copolymers; and films or sheets thereof. Furthermore, in these hot melt based resins or films or sheets thereof, ones having various additives (for example, an antioxidant) compounded therein can be used. In particular, low density polyethylene and polyethylene obtained by using a metallocene catalyst are useful.

In the case of interposing a heat generating composition molded body between a substrate and a covering material, the "temporary adhesion" as referred to in the invention means weak pressure-sensitive bonding or adhesion for the purpose of holding the accommodated heat generating composition molded body until at least the substrate and the covering material are adhered to each other via a sticky layer made of an adhesive and heat sealed.

Furthermore, the "deadhesion" as referred to herein means that in the temporary adhering seal part after heat seal, the heat generating composition in a non-heat sealed region is transferred to the foregoing region, thereby releasing the temporary adhesion.

The temporary adhering seal part is formed via a sticky layer. An adhesive constituting the sticky layer is not limited so far as it is a layer formed of a polymer composition which is tacky at the normal temperature and can be heat sealed after the temporary adhesion.

Furthermore, although the adhesive of the foregoing adhesive layer can be used as the adhesive constituting the sticky layer to be used for the temporary adhesion, a non-hydrophilic adhesive is preferable. As the adhesive constituting the sticky layer, one which is well compatible with the heat seal material constituting the heat seal is preferable, and a melting point of a base polymer of the adhesive is preferably not higher than a melting point of the heat seal material. In particular, hot melt based adhesives are preferable. Furthermore, in the case where the heat seal material is made of an olefin based raw material, preferred examples of the adhesive include olefin based adhesives.

Incidentally, a method for providing a sticky layer for the temporary adhesion is not limited. The sticky layer may be entirely provided or partially or intermittently provided. Examples of its shape include various shapes such as a network-like shape, a stripe-like shape, a dot-like shape, and strip-like shape.

Each of the substrate, the covering material and the adhesive layer constituting the heat generating body may be transparent, opaque, colored, or colorless. Furthermore, a layer constituting at least one layer of the layers constituting the respective materials and layers may be colored to a color different from those of other layers.

The heat generating body may be accommodated in an outer bag which is an air-impermeable accommodating bag, stored and transported. The outer bag is not limited so far as it is air-impermeable and may be made of a laminate. Examples thereof include a heat generating body prepared by interposing a produced heat generating body between two sheets of an air-impermeable film or sheet, punching the two sheets of film or sheet into a size larger than that of the heat generating body at the same time with or after this interposition, and sealing the two sheets of film or sheet in the surroundings exceeding the size of the heat generating body at the same time with or after this punching.

The heat generating body may be accommodated in an outer bag which is an air-impermeable accommodating bag, stored and transported. The outer bag is not limited so far as it is air-impermeable and may be made of a laminate. Examples thereof include a heat generating body prepared by interposing a produced heat generating body between two sheets of an air-impermeable film or sheet, punching the two sheets of film or sheet into a size larger than that of the heat generating body at the same time with or after this interposition, and sealing the two sheets of film or sheet in the surroundings exceeding the size of the heat generating body at the same time with or after this punching.

In the production process of the heat generating body of the invention, plural heat generating composition molded bodies resulting from molding a moldable heat generating composition containing surplus water as a connecting substance by a molding system such as a force-through die molding method and a cast molding method, laminating them at intervals on a substantially planar substrate which does not have an accommodating pocket, putting a covering material thereon, and sealing the surroundings of the heat generating composition molded bodies, thereby providing a sectional exothermic part. The sectional exothermic part is provided in a plural number, the respective sectional exothermic parts are separated from each other by a sectioned part which is a heat seal part and disposed, and an exothermic part is formed by a gathering of the sectional exothermic parts. Furthermore, the outermost surroundings of the respective sectional exothermic parts adjacent to the surroundings of the heat generating body are heat sealed, too. Next, the heat generating body is produced via a cutting step, etc. The sealing step, the cutting step and the like may be properly selected and employed from conventional methods and devices.

Furthermore, in the seal step, the seal is not limited so far as seal is possible. Usually, heat seal or compression seal or a mixture thereof is employed. The surface of the seal part may be of a plain shape or a patterned shape whose cross-sectional shape is irregular, and a mixture of a plain shape and a patterned shape whose cross-sectional shape is irregular. The mixture of pattern as referred to herein means a mixture of a plain shape in the inside of the seal part and a patterned shape in the outside of the seal part, or a mixture of a patterned shape in the inside of the seal part and a plain shape, a partially plain shape or a partially patterned shape in the outside of the seal part. Furthermore, the back side may be plain, with the front side being patterned, and vice versa. Furthermore, a part or the whole of the pattern may be a double pattern. Accordingly, following this, a plain or patterned seal roll is used as a seal roll. Furthermore, a pair of seal rolls may be used. Multiplex seal may be carried out by placing plural seal rolls of two or more. Examples of the multiplex seal include duplex seal, triplet seal, quadruplet seal, and quintuplet seal. The width of seal may be the same or different and may be properly determined. In the case of high-speed seal, a higher number of multiplex seal is preferable. In the case of using a seal roll or a compression seal roll to which the temperature is applied, the temperature of a pair of rolls may be the same, or the temperature of one roll may be different from that of the other roll.

The "force-through die molding" as referred to herein means a continuous formation method in which by using a molding machine for using a molding die and laminating a heat generating composition molded body having a shape of the molding die on a longitudinal substrate and a rotary sealer capable of covering the laminate by a longitudinal covering material and sealing (for example, heat seal, compression seal, and heat compression seal) a desired sectioned part and the substrate together with the surroundings of the covering material, the surroundings of the heat generating composition molded body and a necessary place of the sectioned part are heat sealed, thereby achieving a sealing treatment.

Furthermore, a magnet may be used for molding the moldable heat generating composition of the invention. By using a magnet, it becomes possible to easily achieve accommodation of the heat generating composition in a die and separation of the molded body from the die, thereby making it easier to mold a heat generating composition molded body.

The "cast molding method" as referred to herein means a molding method for laminating a heat generating composition molded body on a longitudinal substance by filling in a casting mold having a concave and transferring into a substrate. In the continuous case, there is enumerated a continuous formation method in which by using a molding machine for laminating a heat generating molding molded body on a longitudinal substrate by filling in a concave and transferring into a substrate by a drum-type rotary body and a rotary sealer capable of covering the laminate by a longitudinal covering material and sealing (for example, heat seal, compression seal, and heat compression seal) a desired sectioned part and the substrate together with the surroundings of the covering material, the surroundings of the heat generating composition molded body and a necessary place of the sectioned part are heat sealed, thereby achieving a sealing treatment.

Incidentally, the heat generating body may be produced by providing an air-permeable sticky layer at least between the heat generating composition molded body and the covering material or providing an underlay material such as non-woven fabrics between the heat generating composition molded body and the covering material. In the case of providing an air-permeable sticky layer at least between the heat generating composition molded body and the covering material, there is no limitation so far as an air-permeable sticky layer is present at least between the heat generating composition molded body and the covering material. For example, the air-permeable sticky layer may be provided on the surface of the covering material opposing to the heat generating composition molded body; and the air-permeable sticky layer may be provided on the heat generating composition molded body or a laminate of the heat generating composition molded body and the substrate and temporarily adhered under pressure or the like between the covering material and the heat generating composition molded body and/or the substrate.

Furthermore, after temporarily adhering the covering material and the substrate and/or the heat generating composition molded body by the sticky layer among the heat generating composition molded body, the substrate and the covering material, the surroundings of the heat generating composition molded body and the surroundings of the heat generating body may be heat sealed. In this way, the heat generating composition molded body becomes stable; real sealing by heat sealing becomes easy; seal deviation or the like does not occur; high-speed sealing becomes possible; and it becomes possible to realize a high-speed production process of a heat generating pad.

Here, as a process for producing a heat generating body in which an absolute value of a difference between bending resistances in the two directions as substantially orthogonal directions becomes maximal, there is enumerated a production process in which a heat generating composition molded body having a size of 120 mm in long side length×6 mm in short side length is prepared by force-through molding; 12 heat generating composition molded bodies are laminated substantially in parallel at intervals of 10 mm on a substrate made of a laminate of a nylon-made non-woven fabric and a polyethylene film; an air-permeable covering material made of a laminate of a nylon-made non-woven fabric and a polyethylene-made porous film is put thereon; the surroundings of 2 mm outside the periphery of each of the heat generating composition molded bodies are heat sealed in a width of 4 mm; the outer surroundings of the heat generating body constituted of the respective heat generating composition molded bodies are further heat sealed in a width of 8 mm; and the outer surroundings of the heat generating body are cut while leaving the heat seal. There was thus produced a heat generating body. In a heat generating body as produced by this production process, a ratio of bending resistance is 2 or more, and an absolute value of a difference between bending resistances in the two directions as substantially orthogonal directions becomes maximal. Thus, the heat generating body was very excellent in usefulness.

Here, as a process for producing a heat generating body in which an absolute value of a difference between bending resistances in the two directions as substantially orthogonal directions becomes maximal, there is enumerated a production process in which a heat generating composition molded body having a size of 120 mm in long side length×6 mm in short side length is prepared by force-through molding; 12 heat generating composition molded bodies are laminated substantially in parallel at intervals of 10 mm on a substrate made of a laminate of a nylon-made non-woven fabric and a polyethylene film; an air-permeable covering material made of a laminate of a nylon-made non-woven fabric and a polyethylene-made porous film is put thereon; the surroundings of 2 mm outside the periphery of each of the heat generating composition molded bodies are heat sealed in a width of 4 mm; the outer surroundings of the heat generating body constituted of the respective heat generating composition molded bodies are further heat sealed in a width of 8 mm; and the outer surroundings of the heat generating body are cut while leaving the heat seal. There was thus produced a heat generating body. In a heat generating body as produced by this production process, an absolute value of a difference between bending resistances in the two directions as substantially orthogonal directions becomes maximal. Thus, the heat generating body is very excellent in usefulness.

The "water mobility value" as referred to herein is a value showing an amount of surplus water which can transfer to the outside of the heat generating composition in water present in the heat generating composition. This water mobility value will be described below with reference to FIGS. 9 to 13.

As shown in FIG. 9, a filter paper 13 of No. 2 (second class of JIS P3801) in which eight lines are drawn radiating from the central point with an interval of 45° is placed on a stainless steel plate 17 as shown in FIGS. 10 and 11; a template 14 having a size of 150 mm in length×100 mm in width and having a hollow cylindrical hole 15 having a size of 20 mm in inner diameter×8 mm in height is placed in the center of the filter paper 13; a sample 16 is placed in the vicinity of the hollow cylindrical hole 15; and a stuffer plate 9 is moved on and along the template 14 and inserted into the hollow cylindrical hole 15 while stuffing the sample 16, thereby leveling the sample (force-in die molding).

Next, as shown in FIG. 12, a non-water absorptive 70 μm-thick polyethylene film 12 is placed so as to cover the hole 15, and a flat plate 11 made of stainless steel having a size of 5 mm in thickness×150 mm in length×150 mm in width is further placed thereon and held for 5 minutes such that an exothermic reaction is not caused.

Thereafter, a shown in FIG. 13, the filter paper 13 is taken out, and an oozed-out locus of the water or aqueous solution is read as a distance 18 (unit:mm) from a periphery 19 as an edge of the hollow cylindrical hole to an oozed-out tip along the radiating lines. Similarly, a distance 18 from each of the lines is read, and eight values in total are obtained. Each of the eight values (a, b, c, d, e, f, g and h) which are read out is defined as a measured water content value. An arithmetic average value of the eight measured water content values is defined as a water content value (mm) of the sample.

Furthermore, the water content for the purpose of measuring a real water content value is defined as a compounded water content of the heat generating composition corresponding to the weight of the heat generating composition having a size of 20 mm in inner diameter×8 mm in height or the like, similar measurement is conducted only with water corresponding to that water content, and a value as calculated in the same manner is defined as a real water content value (mm). A value obtained by dividing the water content value by the real water content value and then multiplying with 100 is a water mobility value.

That is, the water mobility value is represented by the following expression.

(Water mobility value)={[Water content value (mm)]/[(Real water content value (mm))]}×100

With respect to the same sample, five points are measured, and the five water mobility values are averaged, thereby defining an average value thereof as a water mobility value of the sample.

Furthermore, in the case of measuring the water mobility value of the heat generating composition in the heat generating body, with respect to the water content for measuring a real water content, a percentage of water content of the heat generating composition is calculated through measurement of the water content of the heat generating composition by an infrared moisture meter, a water content necessary for the measurement is calculated on the basis of the percentage of water content, and a real water content value is measured and calculated from the foregoing water content.

In the invention, a heat generating body can be formed only by laminating a heat generating composition molded body obtained by molding a heat generating composition having surplus water with a water mobility value of from 0.01 to 20 on a substrate, covering a covering material thereon, and sealing at least the periphery of the heat generating composition molded body. After accommodating it in a packaging material such as a substrate and a covering material, it is not necessary to add water. Accordingly, since the process is remarkably simplified, the invention is superior in view of the costs.

In the invention, the water mobility value (0 to 100) is preferably from 0.01 to 20, more preferably from 0.01 to 18, further preferably from 0.01 to 15, still further preferably from 0.01 to 13, even further preferably from 1 to 13, and even still further preferably from 3 to 13.

In a heat generating body using a heat generating composition molded body obtained by molding a moldable heat generating composition containing surplus water as a connecting substance according to the invention, the heat generating composition contains an appropriate amount of surplus water expressed by a water mobility value of from 0.01 to 20 as the connecting substance without using a flocculant aid, a dry binding agent, a flocculating agent, etc.

It is assumed that when the amount of surplus water in the heat generating composition is appropriate, the surplus water causes hydration against hydrophilic groups in the components of the composition due to a bipolar mutual action or hydrogen bond, etc. and that it is present even in the surroundings of hydrophobic groups while having high structural properties. Thus, it is assumed that the heat generating composition becomes in a state of a mud ball, thereby revealing moldability. This is connecting water as a connecting substance in some meaning. Besides, there is water in a state called as free water which can freely move, and it is thought that when the surplus water increases, the structure is softened, whereby the free water increases. Furthermore, controlling factors which an iron powder causes an oxidation reaction are an amount of existing water and a feed amount of oxygen to the surface of the iron powder. It is said that in a degree of water adsorbing film (less than 100 angstroms), the water is not sufficient and that the oxidation rate is small. When the adsorbing film becomes about 1 μm, the water content becomes sufficient. Furthermore, since the thickness of the water film is thin, feed of oxygen onto the surface of the iron powder becomes easy, whereby the oxidation rate becomes large. It is assumed that when the film becomes thicker to an extent that the adsorbing film exceeds 1 μm, the feed amount of oxygen is reduced. The present inventors have obtained knowledge that the water mobility value expressing the optimal water content at which moldability and oxidation rate in fixed levels or more are revealed is from 0.01 to 20, leading to accomplishment of the invention.

That is, by using an appropriate amount of surplus water, the respective component particles are coupled with each other by a surface tension of water, moldability is generated in the heat generating composition, and the water does not substantially function as a barrier layer. Thus, the heat generating composition comes into contact with air to generate heat. In addition, by using a heat generating composition using an active iron powder or an active heat generating composition using an active iron powder, the heat generating composition becomes a heat generating composition having remarkably excellent exothermic rising properties and high moldability. Furthermore, heat generation occurs without causing transfer of the water in the heat generating composition molded body as produced by a molding and laminating system into a packaging material or water absorptive sheet. In addition, by providing plural sectional exothermic parts of the heat generating composition molded body as sectioned by seal parts, it is possible to provide a heat generating body which has flexibility itself, is excellent in installation in places where flexibility is required, such as various places of a human body and curved bodies, and is excellent in feeling for use.

Furthermore, in the substrate, the covering material and the heat generating composition molded body, by temporarily adhering at least the covering material and the heat generating composition molded body to each other via a sticky layer and then heat sealing the periphery of the heat generating composition molded body and the surroundings of the heat generating body, certainty of heat seal is improved so that it becomes possible to design to make the production speed of a heat generating body high and make the heat seal width small.

The "moldability" as referred to in the invention exhibits that a molded body of the heat generating composition having a cavity or concave die shape is formed by force-through molding using a trimming die having a cavity or cast molding using a concave die, whereby after molding including mold release, the molding shape of the heat generating composition molded body is held.

When the moldability is revealed, since the shape is held until the heat generating composition molded article is at least covered by a covering material and a seal part is formed between the substrate and the covering material, sealing can be achieved in the periphery of the shape with a desired shape. Also, since so-called "spots" which are a collapsed piece of the heat generating composition are not scattered in the seal part, the sealing can be achieved without causing cutting in seal. The presence of the spots causes insufficient sealing.

1) Measurement Device:

With respect to the measurement device, a stainless steel-made molding die (a plate having a size of 2 mm in thickness× 200 mm in length×200 mm in width and having a cavity as treated by R5 in four corners of 60 mm in length×40 mm in width in a central part thereof) and a fixable leveling plate are disposed above a travelable endless belt, and magnets (two magnets having a size of 12.5 mm in thickness×24 mm in length×24 mm in width are disposed in parallel) are disposed under the endless belt.

The magnets should cover a region of the leveling plate and the vicinity thereof and a region larger than a region covered by a cut side (40 mm) vertical to the advancing direction of the cavity of the molding die.

2) Measurement Method:

With respect to the measurement method, a stainless steel plate having a size of 1 mm in thickness×200 mm in length× 200 mm in width is placed on the endless belt of the measurement device, a polyethylene film having a size of 70 μm in thickness×200 mm in length×200 mm in width is placed thereon, and a stainless steel-made molding die is further placed thereon.

Thereafter, a leveling plate is fixed in a position of the cavity of the molding die of 50 mm far from the end portion in the advancing direction of the endless belt, 50 g of a heat generating composition is then placed in the vicinity of the leveling plate between the leveling plate and the cavity, and the heat generating composition is filled in the cavity of the molding die while leveling it by moving the endless belt at 1.8 m/min. After the molding die has completely passed through the leveling plate, the traveling of the endless belt is stopped. Next, the molding die is removed, and a heat generating composition molded body as laminated on the polyethylene film is observed.

3) Judgment Method:

With respect to the judgment method, in the surroundings of the heat generating composition molded body, in the case where any collapsed piece of the heat generating composition molded body exceeding a maximum length of 800 μm is not present and the number of collapsed pieces of the heat generating composition molded body having a maximum length of from 300 to 800 μm is not more than 5, it is to be noted that the heat generating composition has moldability.

The moldability is an essential property for a heat generating composition to be used in the molding system. If the heat generating composition does not have moldability, it is impossible to produce a heat generating body by the molding system.

The term "substantially planar" as referred to in the invention means a planar surface not having an accommodating concave such as an accommodating pocket, an accommodating section, and an accommodating zone as provided in advance for the purpose of accommodating the heat generating composition. Accordingly, irregularities which do not intentionally accommodate the heat generating composition may be present.

The "pocket" as referred to in the invention is an accommodating pocket which is provided in advance for the purpose of accommodating the heat generating composition and is a pocket as described in JP-T-2001-507593. Since irregularities which are not used for intentionally accommodating the heat generating composition molded body are not the pocket, even when such irregularities are present on a substrate, it is to be noted that such a substrate is defined as a substantially planar substrate.

The "accommodating section" as referred to herein is an accommodating section for accommodation as provided in advance on the packaging material for the purpose of accommodating the heat generating composition and is an accommodating section as described in Japanese Patent No. 3,161,605 and JP-T-11-508314. Since irregularities which are not used for intentionally accommodating the heat generating composition molded body are not the accommodating section, even when such irregularities are present on a substrate, it is to be noted that such a substrate is defined as a substantially planar substrate.

The "accommodating zone" as referred to herein is an accommodating zone for accommodation as provided in advance on the packaging material for the purpose of accommodating the heat generating composition and is an accommodating zone as described in Japanese Patent No. 3,161,605 and JP-T-11-508314. Since irregularities which are not used for intentionally accommodating the heat generating composition molded body are not the accommodating zone, even when such irregularities are present on a substrate, it is to be noted that such a substrate is defined as a substantially planar substrate.

The "bending resistance" as referred to in the invention exhibits rigidity (tension or nerve) or flexibility and follows the A method according to JIS L1096 (45° cantilever method), except for using a heat generating body itself as a sample. That is, a heat generating body is placed on a horizontal table having a smooth surface and having a slope at an angle of 45° in one end thereof such that one side thereof coincides with a scale base line. Next, the heat generating body is slowly slid toward the slope by an appropriate method, and when a central point of the one end of the heat generating body comes into contact with the slope A, the position of the other end is read by a scale. The bending resistance is exhibited by a length (mm) for which the heat generating body moves. Respective five sheets of heat generating body are measured, and the bending resistance (calculated down to the integral place) is expressed by an average value of lengths measured in the length direction and the width direction, or in one direction and the orthogonal direction thereto. However, in the measurement, in the case of measuring an adhesive layer-provided heat generating body such that the adhesive side is faced at the horizontal table side, while the adhesive side provided with a separator is faced at the horizontal table side. In any way, a measured value in the side at which a minimum bending resistance is measured is employed.

Furthermore, in the measurement, the following must be taken into consideration.

(1) A heat generating composition-incorporated exothermic part of the heat generating body is to retain on the horizontal table to an extent of 5 mm or more in width×20 mm or more in length. However, the length is to cross a region where the heat generating composition is present or to cross linearly a region where the heat generating composition is present and a region where the heat generating composition is not present.

(2) In the case of an adhesive layer-provided heat generating body, a plastic film having a bending resistance of not more than 30 mm, or a limp and soft film such as a limp film having a thickness of not more than 50 μm, and preferably not more than 25 μm and a plastic film in which wrinkles are formed by lightly crumpling is to be used as a separator of the adhesive layer and provided along the adhesive layer. Furthermore, with respect to the bending resistance of the substrate and/or the covering material, a specimen of 100 mm×200 mm is prepared, and a bending resistance in the 200 mm direction is employed.

In the invention, the bending resistance in at least one direction is not more than 200 mm, preferably not more than 100 mm, more preferably not more than 60 mm, further preferably not more than 50 mm, still further preferably not more than 30 mm, and even further preferably not more than 20 mm. Furthermore, the ratio of bending resistance is preferably 2 or more.

A rate of bending resistance of the heat generating body or exothermic part in the invention is a rate of bending resistance to the full length of the heat generating body or exothermic part in one direction and is calculated according to the following expression.

$$(\text{Rate of bending resistance}) = (A/B) \times 100$$

Wherein A represents a bending resistance of the heat generating body or exothermic part in one direction; and B represents the full length of the heat generating body or exothermic part in the foregoing one direction.

In the invention, the rate of bending resistance in at least one direction is usually not more than 50, preferably not more than 40, and more preferably not more than 30.

A ratio of bending resistance in the invention is a ratio of a bending resistance in one direction to a smaller bending resistance in bending resistances in the directions orthogonal thereto in the plane orthogonal to the thickness direction of the heat generating body or exothermic part. The ratio of bending resistance is preferably 2 or more.

In the invention, in the case of a heat generating body having sectional exothermic parts provided at intervals in the striped form, a heat generating body provided with sectional exothermic parts of a parallelepiped shape at intervals in the striped form in which a maximum absolute value of a difference between bending resistances in the two directions as intersecting directions, a heat generating body further provided with an adhesive layer, and a heat generating body provided with adhesive layers at intervals in the striped form are very flexible in one direction and rigid in one direction. Thus, these heat generating bodies relieve symptoms such as stiff shoulders, lower-back pain, and muscular fatigue and especially exhibit efficacy for relieving a symptom of menstrual pain. In addition, these heat generating bodies are able to be wound in a size substantially equal to the width dimension in the width direction of the heat generating body, become compact and are convenient for accommodation. Furthermore, in the case of a separator-provided heat generating body, by using a separator having a low bending resistance, winding is possible.

Furthermore, in the case of providing a heat generating body along the body, the body includes many two-dimensional curves, and in shoulders, legs, abdomen, waist, arms, and the like, one direction is substantially linear, and the other two directions are formed of a substantially curved surface. Accordingly, since the heat generating body of the invention which is able to form a substantially linear surface in one direction and a curved surface in the other two directions is able to form a two-dimensional curved surface, it is able to well follow the body and is optimum for warming of the body and relaxation or treatment of various symptoms.

Furthermore, in the heat generating body of the invention, by adjusting the size or space of the convex sectional exothermic part, an exothermic part which is flexible and exhibits a uniform temperature distribution or an exothermic part exhibiting a pattern-like temperature distribution is obtainable. By the pattern-like temperature distribution, it is possible to improve a meridian effect of the warming part.

In the heat generating body having sectional exothermic parts, a minimum bending resistance of the bending resistance on the surface orthogonal to the thickness direction is preferably not more than 50 mm, more preferably not more than 40 mm, further preferably not more than 30 mm, and still further preferably from 5 to 30 mm.

The bending resistance and ratio of bending resistance are kept at least at a temperature between 20° C. and 60° C.

The "water retention" as referred to herein is a value as measured and calculated in the following method. That is, about 1 g of a sample fiber as prepared by cutting into a length of about 5 cm and well opening is dipped in pure water, and after elapsing 20 minutes (at 20° C.), water among the fibers is removed using a centrifuge by revolution at 2,000 rpm. A weight (W1) of the thus prepared sample is measured. Next, the sample is dried in a vacuum dryer at 80° C. until it becomes constant in weight, thereby measuring a weight (W2). A water retention is calculated according to the following expression.

[Water retention (%)]=[(W1−W2)/W2]×100

In the invention, the water retention is preferably 20% or more.

In the tensile test of the invention, the packaging material is cut into a size of 2.5 cm in width×about 20 cm in length according to JIS L1096. A sample is applied with a tensile force sufficient for eliminating all relaxations in ends of the small piece without applying a load to a load cell, nipped by a chuck with a chuck interval of 10 cm, and placed in a unit. Next, the temperature of the sample is stabilized at a desired test temperature.

(1) Judgment Test of Non-Elastic Body:

After stabilizing the sample at 25° C., the chuck interval is elongated by 5 mm at a cross head speed of about 50 cm/min, and the sample is then taken out from the unit.

In the case where the length after elongation is longer than that before the elongation, a permanent set is generated, and therefore, such a sample is defined as a non-elastic body.

Furthermore, a sample which generates a deviation from the linear function relation between elongation and tensile strength and is admitted to fall outside the elastic deformation is also defined as a non-elastic body.

Furthermore, in an anisotropic sample, a sample which is admitted to be non-elastic in at least one direction is defined as a non-elastic body.

(2) Breaking Strength at 25° C.:

After stabilizing at a test temperature of 25° C., a unit is operated until the sample is broken, and when broken, a strength of the sample is read from a chart and defined as a breaking strength at 25° C.

(3) Breaking Strength at 90° C.:

After stabilizing at a test temperature of 90° C., a unit is operated until the sample is broken, and when broken, a strength of the sample is read from a chart and defined as a breaking strength at 90° C.

(4) Breaking Elongation at 90° C.:

After stabilizing at a test temperature of 90° C., a unit is operated until the sample is broken, and when broken, an elongation of the sample is read from a chart and defined as a breaking elongation at 90° C.

According to JIS L1096, a sample having a size of 2.5 cm in width×20 cm in length is nipped by a chuck with a chuck interval of 10 cm and elongated at a cross heat speed of about 50 cm/min until the chuck interval is increased by 5 mm by a tensile test at the circumferential temperature. When a sample after the test generates a permanent set in the elongation direction, or a sample which generates a deviation from the linear function relation between elongation and tensile strength and is admitted to fall outside the elastic deformation is also defined as a non-elastic body. Furthermore, in an anisotropic sample, a sample which is admitted to be non-elastic in at least one direction is defined as a non-elastic body.

The term "elastic" as referred to herein means a characteristic of a material such that when receiving a tensile force, the material is elongated or widened in the direction of the force, and when eliminating the force, it is returned to the original dimension.

More concretely, the term "elastic" means a directional characteristic such that an element or a structure receives a percentage strain H % exceeding 50% and is then recovered within about 10% of the original length Lb.

The percentage strain H % as used in this specification is defined as follows.

$$H\% = [(Lx-Lb)/Lb] \times 100$$

In the foregoing expression, Lx represents a length when elongated; and Lb represents an original length.

In order to make consistent comparison, it is preferable that the recovery of the element or structure is measured within 30 seconds after relieving from the length Lf at the time of elongation. When the element or structure is not recovered to the range within about 10% within 30 seconds after relieving from 50% of a percentage strain H %, it is considered that such an element or structure is all non-elastic. The non-elastic element or structure also include an element or structure which when receiving 50% of a percentage strain H %, breaks and/or deforms permanently or reversibly.

The term "non-shrink properties at 90° C." as referred to herein means that after holding at 90° C. for 3 minutes and then returning to room temperature, the length does not become shorter than the original length. In more detail, the term "non-shrink properties at 90° C." means that after holding at 90° C. for 3 minutes and then returning to room temperature, a shrinkage factor is preferably not more than 15%, more preferably not more than 10%, further preferably not more than 8%, still further preferably not more than 5%, and even further preferably not more than 1%.

This shrinkage factor is defined as follows.

$$S=[(Lb-L90)/Lb]\times 100$$

In the foregoing expression, S represents a shrinkage factor (%); Lb represents an original length; and L90 represents a length after holding at 90° C. for 3 minutes and then returning to room temperature.

In particular, it is preferable that in the case of laminating a heat generating composition molded body (also including a heat generating composition compressed body in the invention) on a packaging material not having an accommodating pocket by molding with a die, further covering a packaging material thereon and then sealing the laminate to prepare an exothermic part or heat generating body having a sectional exothermic part, a laminate of a thermoplastic resin-made fibrous material and a thermoplastic resin-made film-like material is used for at least one of the packaging materials.

As the packaging material for heat generating body by molding with a die, a packaging material which is flexible but non-elastic at least at from 25 to 60° C., preferably has a breaking strength of 400 g/mm² or more, more preferably 500 g/mm² or more, and further preferably 800 g/mm² or more at 25° C., and preferably has a breaking elongation of 20% or more, more preferably 30% or more, further preferably 50% or more, still further preferably 100% or more, and even further preferably 150% or more at 90° C. is preferable. In this way, since in heat sealing the periphery of the heat generating composition molded body, the packaging material can be elongated by remaining heat to an extent necessary for heat sealing, the periphery of the heat generating composition molded body can be heat sealed without causing cutting in seal, and the shape of the heat generating body can be kept at the time of using the heat generating body.

The "film-like material" as referred to herein means a film of the raw material as described above in the substrate or covering material. Examples of the fibrous material include non-woven fabrics and woven fabrics. The lamination method is not limited. Examples of the method include one used in the production of a packaging material to be used for a heating material such as a chemical warmer.

The term "extensible" as referred to herein means a property such that when a tensile force is given, the material is stretched without causing breakage, especially it can be stretched to an extent of 1.1 times or more of the original length. It does not matter whether or not when this tensile force is eliminated, the material returns to the original state.

Examples of the extensible material include extensible films, sheets, non-woven fabrics, kited fabrics, woven fabrics, and laminates thereof. Its thickness is not particularly limited so far as when a tensile force is given to a flexibility-holding part as formed by using such a material, the flexibility-holding part is stretched to an extent of 1.2 times or more of the original length without causing breakage. Examples thereof include synthetic resin-made single-layered films and synthetic resin-made laminates.

For example, though the thickness of the synthetic resin-made single-layered film is not limited, it is preferably not more than 15 μm, and more preferably from 5 to 12.5 μm. When the thickness exceeds 15 μm, desired extension properties may not be possibly obtained.

The non-extensible material is a material other than the foregoing extensible material.

The term "stretchable" as referred to herein exhibits a characteristic such that when a tensile force is given, the material is stretched in the direction of the force without causing breakage and when the tensile force is eliminated, the material returns to the original length when no tension is applied.

It is preferable that at least one of the foregoing packaging materials is made of a raw material preferably having a breaking strength of 400 g/mm² or more, more preferably 500 g/mm² or more, further preferably 1,000 g/mm² or more, and still further preferably 2,000 g/mm² or more at 25° C. and having a breaking elongation of 100% or more at 90° C. Furthermore, though the thickness of the packaging material is not limited so far as the foregoing breaking elongation is secured, it is preferably 10 μm or more, more preferably from 10 to 500 μm, further preferably 10 to 300 μm, still further preferably from 10 to 250 μm, and even further preferably from 50 to 250 μm.

Laminates of a non-woven fabric and a film-like material of a thermoplastic resin are preferably enumerated.

At least one packaging material is a laminate of a fibrous material and a film-like material and is made of a raw material which is heat sealable and flexible. Furthermore, this packaging material at least has a breaking strength of 500 g/mm² or more under circumstances of from 25 to 60° C. and a breaking elongation of 100% or more at 90° C. In a heat generating body using this packaging material of the invention, the sectional exothermic parts containing a heat generating composition molded body or a heat generating composition compressed body as a compressed body of the heat generating composition molded body have a high bending resistance, and the sectioned parts as a heat seal part, which are present therebetween and do not contain a heat generating composition molded body or a heat generating composition compressed body (hereinafter referred to as "heat generating composition molded body") as a compressed body of the heat generating composition molded body have a low bending resistance. Since the exothermic part comprising a sectional exothermic part and a sectioned part can keep the bending resistance at a temperature of from about 0° C. to about 80° C., the sectioned part functions as a hinge and is preferentially bent over the sectional exothermic part. In the heat generating body comprising a sectional exothermic part and a sectioned part, the sectioned part at least functions as a hinge at from the normal temperature to the temperature at the time of heating (from about 23° C. to about 50° C.) and is preferentially bent over the sectional exothermic part. A satisfactory difference of bending resistance at the time of heating is still kept. As a result, the heat generating body keeps structural support of the sectional exothermic part and has sufficient rigidity during the production or during the use. On the other hand, the excellent bending resistance at the time of heating is still kept.

In the heat generating body using the foregoing packaging material for at least one of the substrate or covering material, the heat generating composition molded body is laminated on a substantially planar substrate, a covering material is covered thereon, and the periphery of the heat generating composition molded body is heat sealed, thereby forming a sectioned part as a seal part. For example, in the case of using the foregoing packaging material for a covering material, since the packaging material is flexible and has a breaking strength of 500 g/mm$^2$ or more at 25° C. at least at from 25 to 60° C., though it is bent, it has nerve and is able to surely cover the heat generating composition molded body. In addition, since the covering material has a breaking elongation of 100% or more at 90° C. at the time of heat seal, the covering material does not cause breakage by the temperature at the time of heat seal, is free from cutting in seal, and is able to surely form a heat seal part. Accordingly, in the heat generating body of the invention having an exothermic part comprising a sectional exothermic part containing a heat generating composition molded body and a sectioned part not containing a heat generating composition molded body, the sectional exothermic parts containing a heat generating composition molded body or a heat generating composition compressed body as a compressed body of the heat generating composition molded body have a high bending resistance, and the sectioned parts as a heat seal part, which are present therebetween and do not contain a heat generating composition molded body or a heat generating composition compressed body as a compressed body of the heat generating composition molded body have a low bending resistance. Since the exothermic part comprising a sectional exothermic part and a sectioned part can keep the bending resistance at a temperature of from about 0° C. to about 80° C., the sectioned part functions as a hinge and is preferentially bent over the sectional exothermic part. Since the heat generating body comprising a sectional exothermic part and a sectioned part uses at least a packaging material which is small in change at the temperature of use, dimensional changes due to the packaging material are small at the time of use, and structural flexibility due to the bending resistance are kept. Thus, stable and appropriate flexibility is kept in the heat generating body. Furthermore, since in at least one of the packaging materials, a packaging material (usually a covering material) having a breaking elongation of 100% or more at 90° C. is used, in the case of covering a substantially planar covering material on a heat generating composition molded body as laminated on a substantially planar substrate and heat sealing the periphery of the heat generating composition molded body, wrinkles which generate seal leakage are not generated so that a seal part free from cutting in seal can be formed. The covering material can partly have a convex.

The air-permeable covering materials as used in the foregoing Examples were all a non-elastic body having a permanent elongation of from 0.5% to 1.7% at a temperature between 25° C. and 60° C. and were a laminate having a breaking strength of 400 g/mm$^2$ or more at 25° C. and a breaking elongation of 20% or more at 90° C.

The "seal strength at 60° C." as referred to herein means an average value of respective maximum values obtained by subjecting three samples to a measurement by taking a specimen of 25 mm×250 mm from a place of a subjective sealed sample to be measured for the seal strength, allowing the specimen to stand under circumstances at 60° C. for 5 minutes, grasping it under circumstances at 60° C., and measuring a maximum strength at intervals of 10 mm and at a tensile speed of 300 mm/min.

The seal strength of the temporary adhering part is preferably 0.5 kg/25 mm or more, more preferably from 0.5 to 1 kg/25 mm, further preferably from 0.5 to 0.9 kg/25 mm, and still further preferably from 0.5 to 0.8 kg/25 mm under circumstances at 20° C.; and the seal strength at 60° C. is preferably less than 0.8 kg/25 mm, more preferably 0.01 kg/25 mm or more but less than 0.8 kg/25 mm, further preferably 0.01 kg/25 mm or more but less than 0.5 kg/25 mm, and still further preferably 0.01 kg/25 mm or more but less than 0.4 kg/25 mm.

The sticky layer of the temporary adhering part is constituted of an adhesive, has a seal strength at 60° C. of from 0.01 to 0.8 kg/25 mm, is able to stop the movement of the heat generating composition molded body between the substrate and the covering material, and makes it possible to achieve high-speed heat seal. In addition, if desired, warming may be carried out at the time of temporary adhesion. It is preferable that the warming is carried out under pressure at a temperature of not higher than a melting point of a base polymer in a hot melt based adhesive for forming the adhesive layer.

The seal strength under circumstances at 20° C. of the heat seal part which has been heat sealed after the temporary adhesion is preferably 1.0 kg/25 mm or more, more preferably 1.2 kg/25 mm or more, further preferably 1.5 kg/25 mm or more, and still further preferably from 1.5 to 3 kg/25 mm. Furthermore, the seal strength at 60° C. under circumstances at 60° C. is preferably 0.8 kg/25 mm or more, more preferably 1.0 kg/25 mm or more, further preferably 1.2 kg/25 mm or more, and still further preferably 1.5 kg/25 mm or more. Here, the condition of the seal strength under circumstances at 20° C. is identical with that of the seal strength at 60° C., except that the circumferential temperature for the measurement is 20° C.

Next, specific shapes of the invention will be described with reference to FIGS. 1 to 8.

FIG. 1 is a plan view of a heat generating body 1 having a broad bean-like shape, in which plural sectional exothermic parts 3 are provided in a striped form via a heat sealed sectioned part 4. Incidentally, in the drawing, 5 is a seal part of the periphery of the heat generating body 1. Furthermore, FIG. 2 is a cross-sectional view along the line Z-Z of FIG. 1; and FIG. 3 is a plan view of the heat generating body 1 of FIG. 1. In the drawings, 9 is a separator.

FIG. 4 is a plan view to show an embodiment of a heat generating body of a paper lantern-like shape, in which sectional exothermic parts 3 are continuously provided in a striped form and the sectional exothermic part 2 is not provided in the vicinity of the central part. The foregoing heat generating body 1 is used for shoulder and hung on the shoulder, and the heat generating body 1 is patched on the skin of the shoulder via a sticky layer in every end part. At this time, the heat generating body 1 is well fit along the shoulder, does not cause deviation or falling-off during the use and is excellent in a feeling for use. Furthermore, FIG. 5 is a cross-sectional view along the line Y-Y of FIG. 4.

FIG. 6 is a plan view of a heat generating body 1 having a broad bean-like shape, which is composed of elliptical convex sectional exothermic parts 3 and convex sectioned parts 4.

FIG. 7 shows a heat generating body 1 of a paper lantern-like shape having circular convex sectional exothermic parts 3 and convex sectioned parts 4, in which the sectional exothermic parts 3 are provided at intervals in the vicinity of the central part such that it can be bent between the sectional exothermic parts 3, 3. Incidentally, an adhesive layer 8B which is a fixing measure is provided in every end part of the heat generating body 1, and a separator 8 is provided thereon.

FIGS. 8(a) to 8(q) show modifications of the shape of the heat generating body of the invention. (a) shows a broad bean-like shape; (b) shows an eye mask-like shape; (c) shows a cocoon-like shape; (d) shows a gourd-like shape; (e) shows a rectangular shape with rounded corners; (f) shows a rectangular shape; (g) shows a square shape with rounded corners; (h) shows a square shape; (i) shows an egg-like shape; (j) shows a boomerang-like shape; (k) shows a comma-shaped bead-like shape; (l) shows a star-like shape; (m) shows a wing-like shape; (n) shows a wing-like shape, too; (o) shows a nose-like shape; (p) shows a paper lantern-like shape; and (q) shows a paper lantern-like shape, too, respectively.

The invention will be described below with reference to the following Examples, but it should not be construed that the invention is limited thereto.

DESCRIPTION OF REFERENCE NUMERALS AND SIGNS

Figure 1:
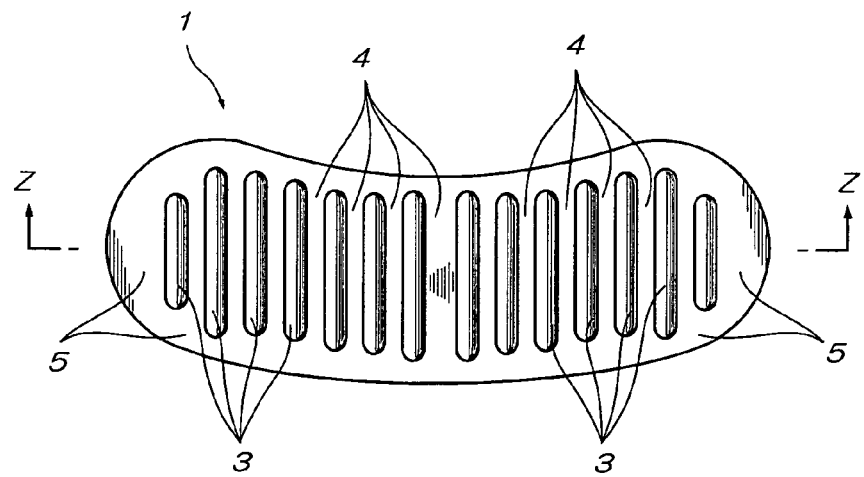
FIG. 1 is a plan view of an embodiment of the heat generating body of the invention.

1: Heat generating body
2: Heat generating composition
3: Sectional exothermic part
4: Sectioned part
5: Circumferential seal part
6: Substrate
7: Covering material
8: Adhesive layer
9: Separator
10: Pushing plate
11: Flat plate
12: Non-water absorptive film (for example, a polyethylene film)
13: Filter paper in which eight lines are drawn radiating from the central point with an interval of 45°
14: Die plate having a hollow cylindrical hole
15: Hole
16: Sample
17: Stainless steel plate
18: Distance to the oozed-out locus of water or aqueous solution
19: Position corresponding to a hollow cylindrical hole on filter paper

EXAMPLES

Example 1

Figure 2:
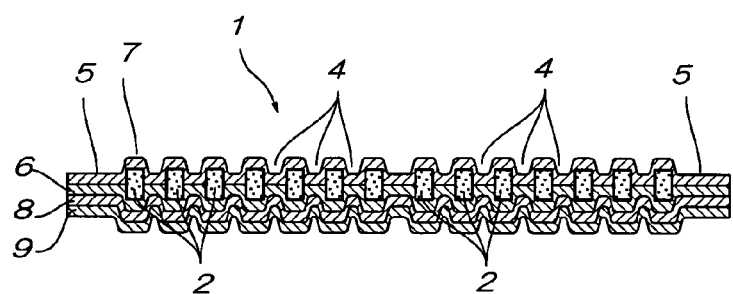
FIG. 2 is a cross-sectional view along the line Z-Z of the same.

This Example will be described below with reference to FIG. 1 and FIG. 2.

A heat generating composition having a water mobility value of 8, which is a mixture consisting of 100 parts by weight of a reduced iron powder (particle size: not more than 300 μm), 7.0 parts by weight of active carbon (particle size: not more than 300 μm), 5.0 parts by weight of a wood meal (particle size: not more than 300 μm), 0.8 parts by weight of a water absorptive polymer (particle size: not more than 300 μm), 0.2 parts by weight of calcium hydroxide, 0.7 parts by weight of sodium sulfite and 11% of salt water, was used.

Next, the heat generating composition was molded by using a trimming die provided with seven cavities in a striped form in each of the right and left sides thereof. Incidentally, the cavities were provided at intervals of 10 mm only in the central part and at intervals of 5 mm in other part, respectively. Also, the dimensions of the cavities were 7 mm in width×80 mm in length.

With respect to the heat generating composition as molded by the trimming die, fourteen heat generating composition molded bodies 2 each constituting a sectional exothermic part 3 were provided on a substrate 6 made of a polyethylene film on which a separator 9 had been laminated via a 30 μm-thick acrylic adhesive layer 8; next, an air-permeable covering material 7 having a nylon-made non-woven fabric with a basis weight of 40 g/m$^2$ laminated on a polyethylene-made porous film was put thereon; and the periphery of each of the heat generating composition molded bodies 2 and the outer surroundings as a heat generating body 1 were sealed. A seal part of the periphery of each of the heat generating composition molded bodies 2 was heat sealed in a seal width of 3 mm. Also, the outer surroundings of the heat generating body 1 were subjected to sealing (5) in a seal width of 8 mm. There was thus obtained a heat generating body 1 having an external dimension of 158 mm in maximum length×98 mm in maximum width. Incidentally, the air permeability of the air-permeable covering material 7 was 400 g/m$^2$/24 hr in terms of moisture permeability by the Lyssy method. Also, the bending resistance of the separator was 20 mm; and the bending resistance of the heat generating body 1 was 30 mm in the long side direction (the direction orthogonal to the stripe direction) and 80 mm or more in the short side direction (the stripe direction) respectively. The ratio of bending resistance was 2 or more. Since the bending resistance in one direction was very high, whereas the bending resistance in a direction substantially orthogonal thereto was very low, the heat generating body was very excellent in handling properties and feeling for use.

Furthermore, since this heat generating body 1 can be wound up, it becomes compact and is convenient for accommodation. Furthermore, as described previously, in the case of providing the separator 9, a separator 9 having a low bending resistance may be used.

The heat generating body 1 was sealed and accommodated in an air-impermeable accommodating bag (hereinafter referred to as "outer bag") and allowed to stand at room temperature for 24 hours. After 24 hours, the heat generating body was taken out from the outer bag, stuck to the outside of a panty and then subjected to an exothermic test for the body. As a result, it was felt warm within 3 minutes, and the warmth was continued for 7 hours. At the same time, curved surface fitness, winding properties and usefulness were evaluated. As a result, the heat generating body was superior in all of these evaluations.

Example 2

A reaction mixture having a water mobility value of less than 0.01, which consists of 100 parts by weight of a reduced iron powder (particle size: not more than 300 μm), 3.5 parts by weight of active carbon (particle size: not more than 300 μm), 4.0 parts by weight of a wool mean (particle size: not more than 300 μm), 2.2 parts by weight of a water absorptive polymer (particle size: not more than 300 μm), 0.2 parts by weight of calcium hydroxide, 0.7 parts by weight of sodium sulfite and 11% salt water, was charged as a heat generating composition in a contact treatment device vessel. Next, the upper portion of the contact treatment device vessel was opened to air, and the reaction mixture was subjected to self heat generation with stirring in the opened state to air under circumstances at 20° C. At a point of time when the temperature rise of the reaction mixture reached 40° C., the reaction mixture was sealed in an air-impermeable accommodating bag and cooled to room temperature, thereby obtaining a heat generating mixture. The heat generating mixture was mixed with 11% salt water, thereby obtaining a heat generating composition having a water mobility value of 12. A covering material 7 the same as in Example 1 was used, and a substrate 6 made of a laminate of a napped non-woven fabric and a polyethylene film was used as the substrate. A trimming die provided with five (ten in total) cavities having 5 mm in width×80 mm in length were respectively provided at intervals of 7 mm in a striped form while interposing the central part in a width of 10 mm was used as the trimming die.

Next, a netlike air-permeable adhesive layer made of an olefin based hot melt based adhesive was provided in the side of the porous film of the air-permeable covering material 7 by a melt blow method and put on heat generating composition molded bodies 2 and the substrate 6. Thereafter, by using a temporary adhering plate, the top of each of the heat generating composition molded bodies 2 and the outside of 8 mm from each of the surfaces of the heat generating composition molded bodies 2 were temporarily adhered in a width of 10 mm linearly in the longitudinal direction. Next, by using a heat seal plate, the surroundings of sectional exothermic parts 3 were sealed in a seal width of 3 mm, and the outer surroundings as a heat generating body 1 were sealed in a seal width of 8 mm, thereby obtaining a heat generating body 1 of 153 mm in length×98 mm in width.

Figure 3:
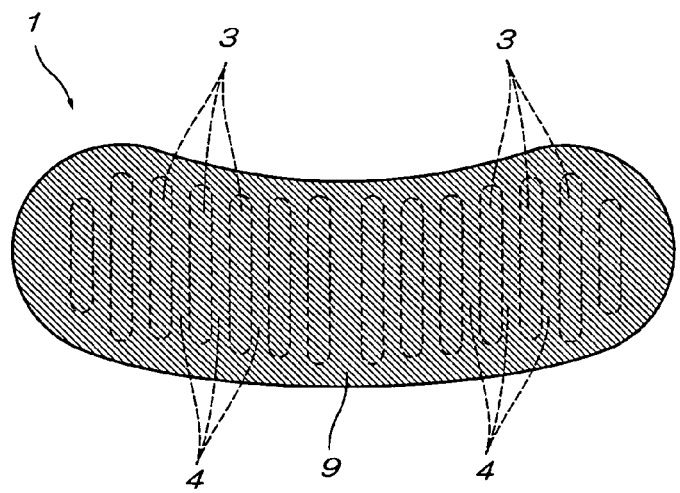
FIG. 3 is a plan view of other embodiment.

Next, as shown in FIG. 3, a netlike hot melt based adhesive layer made of an olefin based hot melt based adhesive was provided on the air-permeable covering material 7 by a melt blow method, and a separator 9 was put thereon, followed by cutting to obtain a heat generating body 1.

The bending resistance of the separator 9 was 20 mm. The bending resistance of the heat generating body 1 was not more than 30 mm in the long side direction of an exothermic part 3 (the direction orthogonal to the stripe direction) and 80 mm or more in the short side direction (the stripe direction), respectively. The ratio of bending resistance was 2 or more. Since the bending resistance in one direction was very high, whereas the bending resistance in a direction substantially orthogonal thereto was very low, the heat generating body was very excellent in handling properties and feeling for use. Furthermore, since this heat generating body 1 could be wound up, it became compact and was convenient for accommodation. Incidentally, in this Example, since the separator having a low bending resistance was used, even the separator-provided heat generating body could be wound up.

The heat generating body 1 was sealed and accommodated in an air-impermeable outer bag and allowed to stand at room temperature for 24 hours. After 24 hours, the heat generating body 1 was taken out from the outer bag and then subjected to an exothermic test. As a result, the temperature reached 34° C. within 3 minutes, and the duration of heat generation of 34° C. or higher was long as 8 hours. Furthermore, an exothermic test for the body of the heat generating body was carried out by sticking the heat generating body to the inside of a panty and bringing the side of the napped non-woven fabric into contact with the skin. A temperature characteristic, curved surface fitness, winding properties and usefulness were evaluated. As a result, the heat generating body was superior in all of these evaluations.

Example 3

Figure 4:
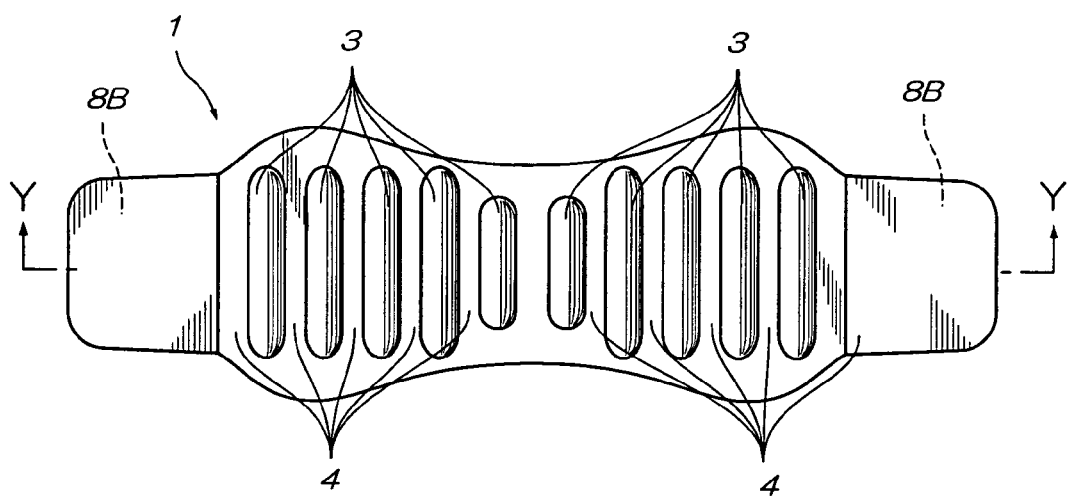
FIG. 4 is a plan view of other embodiment of the heat generating body of the invention.
Figure 5:
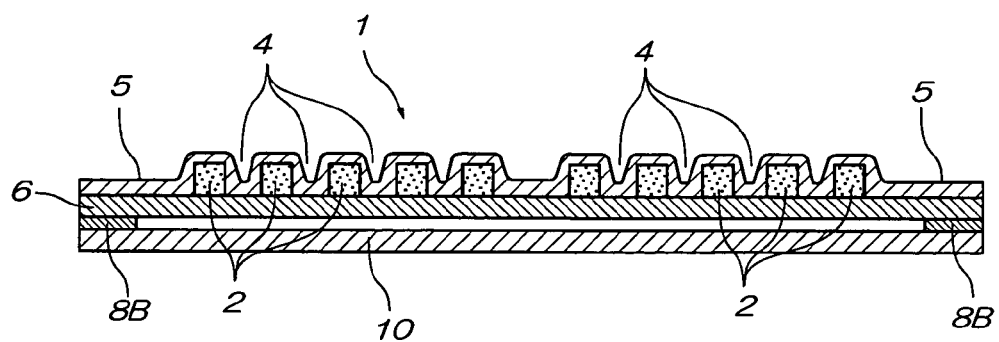
FIG. 5 is a cross-sectional view along the line Y-Y of the same.

As shown in FIG. 4 and FIG. 5, a heat generating body 1 in a paper lantern-like shape having striped sectional exothermic parts 3 was produced in the same manner as in Example 2. However, in this Example, a pressure sensitive adhesive double coated tape was provided as an adhesive layer 8B on the surface opposite to the air-permeable surface in every end part in the longitudinal direction. The heat generating body 1 was fixed to a shoulder by the adhesive layers 8B and then subjected to an exothermic test for the body. As a result, the heat generating body had good adaptability to the shoulder. Furthermore, a temperature characteristic, curved surface fitness, winding properties and usefulness were evaluated. As a result, the heat generating body was superior in all of these evaluations.

Example 4

The same procedures as in Example 1 were followed, except that the reduced iron powder was changed to an iron powder (particle size: not more than 300 μm) containing 0.21% by weight of a carbon component, as prepared by subjecting a sponge iron to a covering treatment with 1% by weight of active carbon.

Figure 6:
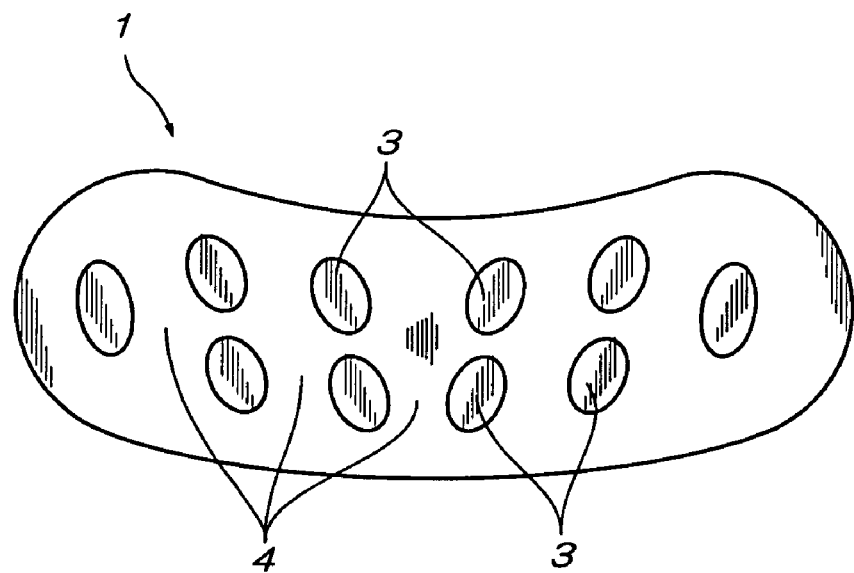
FIG. 6 is a plan view of other embodiment of the heat generating body of the invention.

Then, as shown in FIG. 6, a heat generating body 1 in a broad bean-like form having elliptical sectional exothermic parts 3 was prepared. This heat generating body 1 was subjected to an exothermic test for the body. As a result, the heat generating body was superior in all of evaluations of a temperature characteristic, curved surface fitness, winding properties and usefulness.

Figure 7:
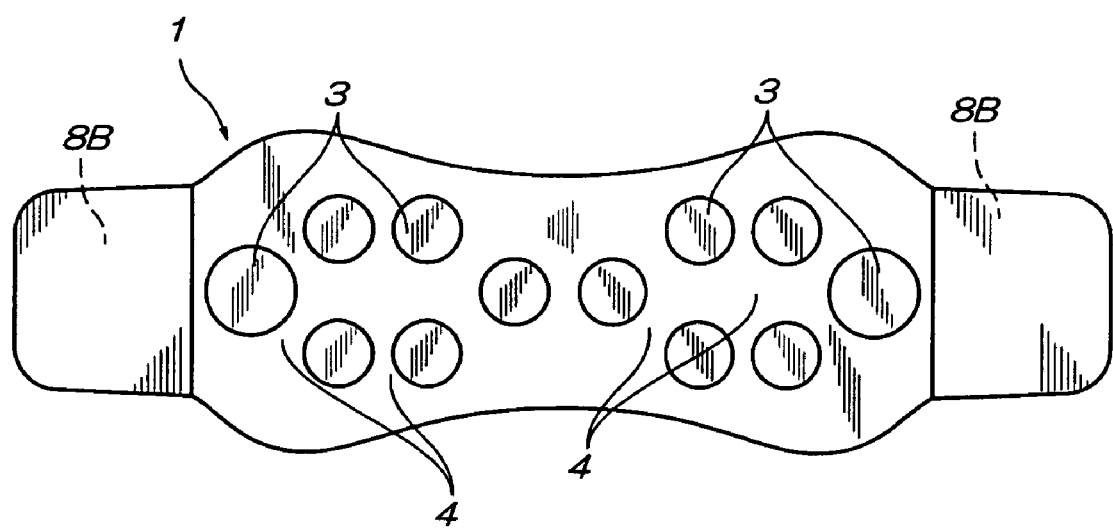
FIG. 7 is a plan view of other embodiment of the heat generating body of the invention.
Figure 8A:
FIG. 8 is a plan view to show modifications of the shape of an embodiment of the heat generating body of the invention.
Figure 8B:
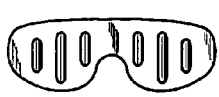
Figure 8C:
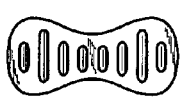
Figure 8D:
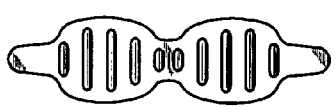
Figure 8E:
Figure 8F:
Figure 8G:
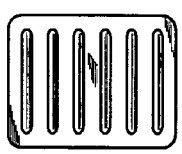
Figure 8H:
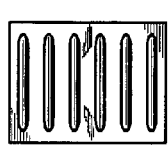
Figure 8I:
Figure 8J:
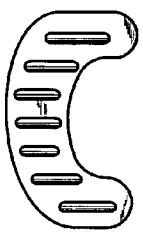
Figure 8K:
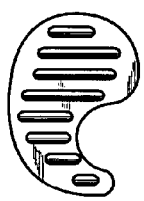
Figure 8L:
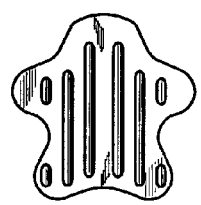
Figure 8M:
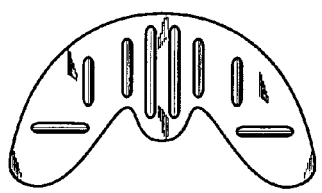
Figure 8N:
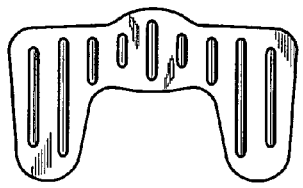
Figure 8O:
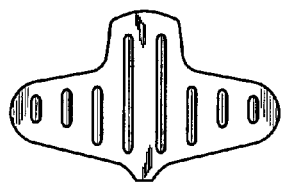
Figure 8P:
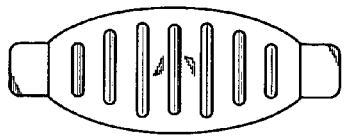
Figure 8Q:
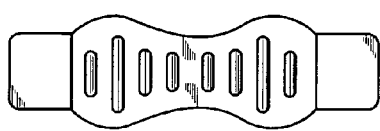
Figure 9:
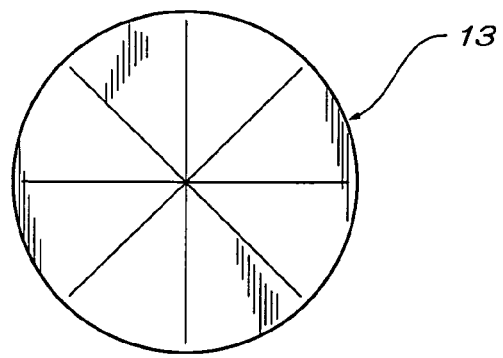
FIG. 9 is a plan view of a filter paper for the measurement of water mobility value in the invention.
Figure 10:
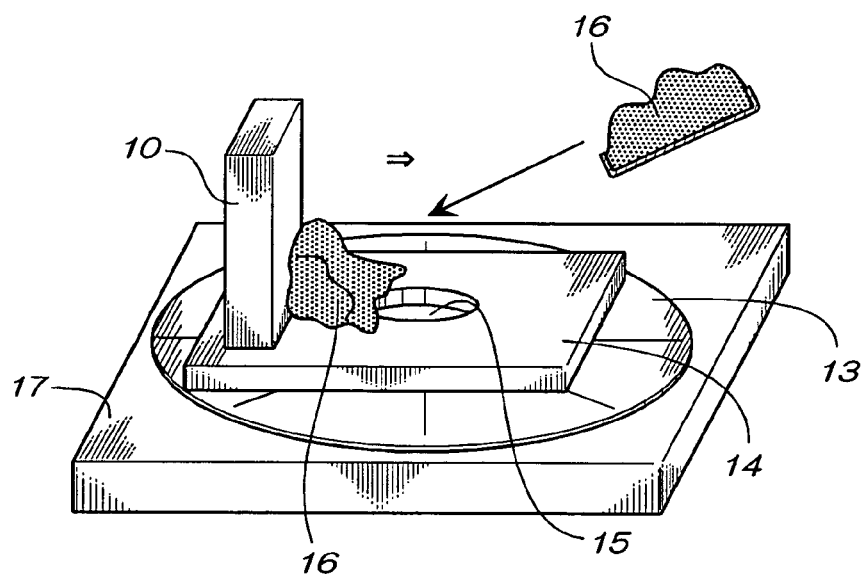
FIG. 10 is an oblique view for explaining the measurement of water mobility value in the invention.
Figure 11:
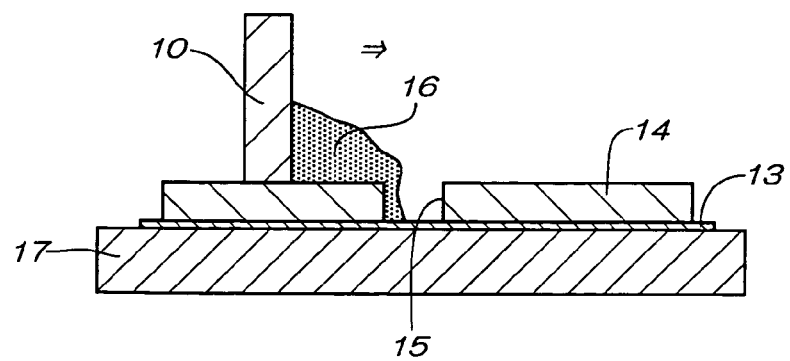
FIG. 11 is a cross-sectional view for explaining the measurement of water mobility value in the invention.
Figure 12:
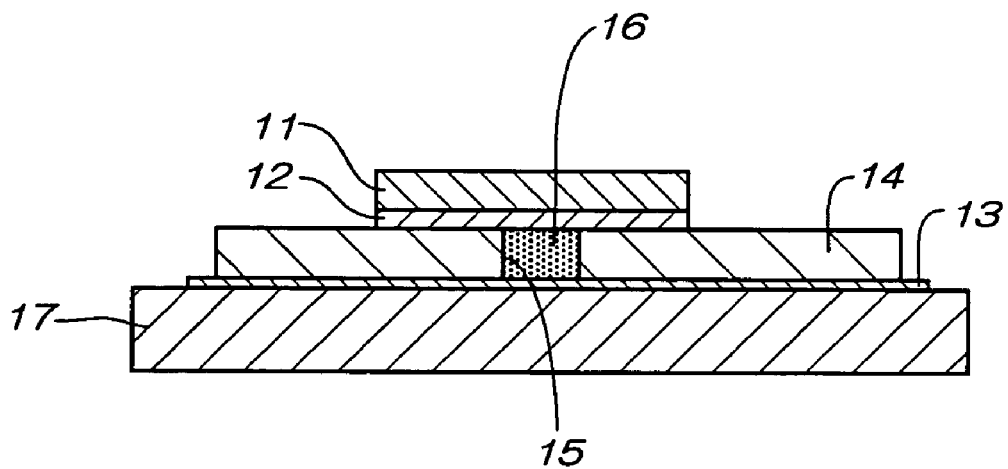
FIG. 12 is a cross-sectional view for explaining the measurement of water mobility value in the invention.
Figure 13:
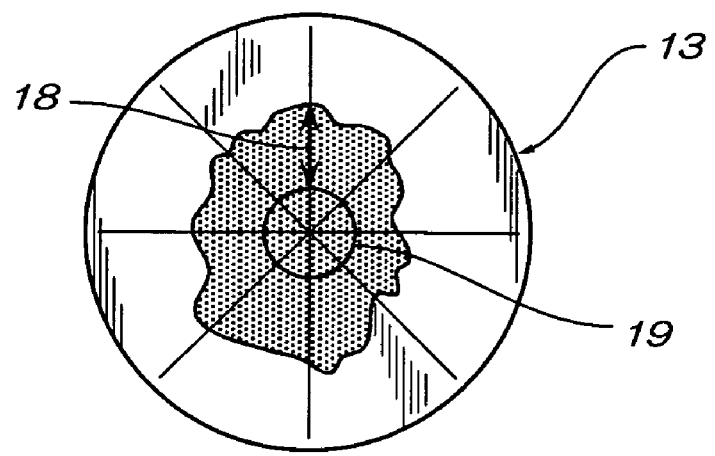
FIG. 13 is a plan view of a filter paper after carrying out the measurement of water mobility value in the invention.

As shown in FIG. 7, a heat generating body 1 in a paper lantern-like shape having circular sectional exothermic parts 3 was produced. This heat generating body 1 was subjected to an exothermic test for the body. As a result, the heat generating body was superior in all of evaluations of a temperature characteristic, curved surface fitness, winding properties and usefulness.

Incidentally, the air-permeable covering materials as used in Examples 1 to 4 were all a non-elastic body having a permanent elongation of from 0.5% to 1.7% at a temperature between 25° C. and 60° C. and were a laminate having a breaking strength of 400 g/mm$^2$ or more at 25° C. and a breaking elongation of 20% or more at 90° C.

The invention claimed is:

1. A heat generating body wherein a heat generating composition molded body resulting from molding a moldable heat generating composition containing surplus water as a connecting substance is interposed between packaging materials and the periphery of the heat generating composition molded body is heat sealed, characterized in that:
   1) the packaging materials are each constituted of a substrate and a covering material,
   2) the substrate, which is substantially planar and does not have an accommodating pocket, has a structure to cover a heat generating composition with the covering material after mounting the heat generating composition on the substantially planar substrate, 3) the packaging materials each has a bending resistance of not more than 100 mm,
4) the packaging materials are each a non-elastic body at least at a temperature between 25° C. and 60° C., has a breaking strength of 500 g/mm² or more at 25° C. and has a breaking elongation of 30% or more at 90° C.,
5) the moldable heat generating composition contains, as essential components, an iron powder, a carbon component, a reaction accelerator and water, has a water content of from 1 to 60% by weight, does not contain a flocculant aid, a flocculant, an agglomeration aid, a dry binder, a dry binding agent, a dry binding material, a sticky raw material, a thickener and an excipient, contains the surplus water so as to have a water mobility value of from 0.01 to 20, has moldability due to the surplus water, with the water in the moldable heat generating composition not functioning as a barrier layer, and is capable of causing an exothermic reaction upon contact with air,
6) plural sectional exothermic parts as divided by a sectioned part which is formed by heat sealing are provided,
7) the heat generating body contains a region wherein the ratio of the bending resistance in a first direction orthogonal to the thickness direction of the heat generating body, to the bending resistance in a second direction orthogonal to the thickness direction of the heat generating body and orthogonal to the first direction, is 2 or more,
8) at least a part of the heat generating body has permeability to air, and
9) the heat generating body has a fixing measure on at least a part of the exposed surface thereof.

2. The heat generating body according to claim 1, characterized in that the packaging materials are each constituted of a laminate of a fibrous material and a film; and that a raw material of each of the fibrous material and the film is a material made of polyethylene inclusive of one as produced using a metallocene catalyst, polypropylene, a nylon, a polyester, polyvinyl chloride, polyvinylidene chloride, polyurethane, polystyrene, a saponified ethyl-ene-vinyl acetate copolymer, an ethylene-vinyl acetate copolymer, a natural rubber, a regenerated rubber, a synthetic rubber, or a mixture thereof.

3. The heat generating body according to claim 2, characterized in that the fibrous material is a non-woven fabric; that the film is a polyethylene-made porous film; and that the non-woven fabric and the polyethylene-made porous film are laminated via an air-permeable sticky layer.

4. The heat generating body according to claim 1, characterized in that the substrate or the covering material is non-shrinkable at 90° C.

5. The heat generating body according to claim 1, characterized in that the packaging materials each has a breaking elongation of 100% or more at 90° C.

6. The heat generating body according to claim 1, characterized in that the heat generating composition contains at least one member selected from additional components consisting of a water retaining agent, a water absorptive polymer, a pH adjusting agent, a hydrogen formation inhibitor, an aggregate, a fibrous material, a functional substance, a surfactant, an organo-silicon compound, a pyroelectric substance, a moisturizer, a fertilizer component, a hydrophobic polymer compound, a heat generating aid, a metal other than iron, a metal oxide other than iron oxide, an acidic substance, and a mixture thereof.

7. The heat generating body according to claim 1, characterized in that the heat seal part is heat sealed after temporary adhesion by an adhesive layer; and that an adhesive component which constitutes the adhesive layer and a component of a heat sealing material which constitutes the heat seal layer are copresent in the heat seal part.

8. A packaging material for die molding which is used in the heat generating body according to claim 1, characterized in that the packaging material is a non-elastic body at least at a temperature between 25° C. and 60° C., has a breaking strength of 500 g/mm² or more at 25° C. and has a breaking elongation of 30% or more at 90° C. and is made of a thermoplastic resin-made fibrous material and a thermoplastic resin-made film.

* * * * *